United States Patent
Takahashi et al.

(10) Patent No.: US 9,049,997 B2
(45) Date of Patent: Jun. 9, 2015

(54) PULSE DETECTOR AND PULSE DETECTION METHOD

(75) Inventors: Yusuke Takahashi, Nagano (JP); Osamu Urano, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 425 days.

(21) Appl. No.: 12/898,966

(22) Filed: Oct. 6, 2010

(65) Prior Publication Data

US 2011/0098582 A1    Apr. 28, 2011

(30) Foreign Application Priority Data

Oct. 27, 2009  (JP) ................................ 2009-246211

(51) Int. Cl.
- *A61B 5/024* (2006.01)
- *A61B 5/00* (2006.01)
- *A61B 5/11* (2006.01)

(52) U.S. Cl.
CPC ............. *A61B 5/024* (2013.01); *A61B 5/721* (2013.01); *A61B 5/11* (2013.01); *A61B 5/7214* (2013.01); *A61B 5/7257* (2013.01)

(58) Field of Classification Search
CPC .... A61B 5/024; A61B 5/7203; A61B 5/7207; A61B 5/721; A61B 5/7214; A61B 5/7217
USPC ................... 600/323–340, 500–503
See application file for complete search history.

(56) References Cited

U.S. PATENT DOCUMENTS

| | | | | |
|---|---|---|---|---|
| 4,238,746 A | * | 12/1980 | McCool et al. | 333/166 |
| 5,285,784 A | * | 2/1994 | Seeker | 600/331 |
| 5,595,176 A | * | 1/1997 | Yamaura | 600/323 |
| 5,742,694 A | * | 4/1998 | Eatwell | 381/94.2 |
| 6,198,951 B1 | * | 3/2001 | Kosuda et al. | 600/323 |
| 6,721,584 B2 | * | 4/2004 | Baker et al. | 600/323 |
| 7,680,652 B2 | * | 3/2010 | Giesbrecht et al. | 704/226 |
| 8,036,728 B2 | * | 10/2011 | Diab et al. | 600/336 |
| 2002/0169381 A1 | * | 11/2002 | Asada et al. | 600/485 |
| 2003/0212336 A1 | * | 11/2003 | Lee et al. | 600/504 |
| 2006/0056502 A1 | * | 3/2006 | Callicotte et al. | 375/232 |
| 2007/0060827 A1 | | 3/2007 | Kobayashi et al. | |

FOREIGN PATENT DOCUMENTS

| | | |
|---|---|---|
| JP | 2001-008908 A | 1/2001 |
| JP | 2003-102694 A | 4/2003 |
| JP | 2005-028157 A | 2/2005 |
| JP | 2005-198829 A | 7/2005 |
| JP | 2007-054471 A | 3/2007 |

OTHER PUBLICATIONS

Basseville et al. "Detection of Abrupt Changes—Theory and Application." Prentice-Hall, Inc. Apr. 1993. 469 pages.*

Cheung, John Y. "Error Smoothing in Adaptive LMS Algorithms." IEEE International Conference on ICASSP '81 Acoustics, Speech, and Signal Processing. Apr. 1981. pp. 901-904.*

V3304 Pulse Oximeter with SAC Technology. Harvard Apparatus.*

* cited by examiner

*Primary Examiner* — Navin Natnithithadha
*Assistant Examiner* — Meredith Weare
(74) *Attorney, Agent, or Firm* — Global IP Counselors, LLP

(57) ABSTRACT

A pulse detector that detects a pulse signal originating from the pulse of a human body includes: a pulse wave sensor that detects and outputs a first pulse wave signal in which the pulse signal and a noise signal are mixed; and a first filtering unit that generates an adaptive spectral line enhancer based on the first pulse wave signal, divides the first pulse wave signal into a first signal and a second signal, and outputs a second pulse wave signal including at least the first signal.

7 Claims, 14 Drawing Sheets

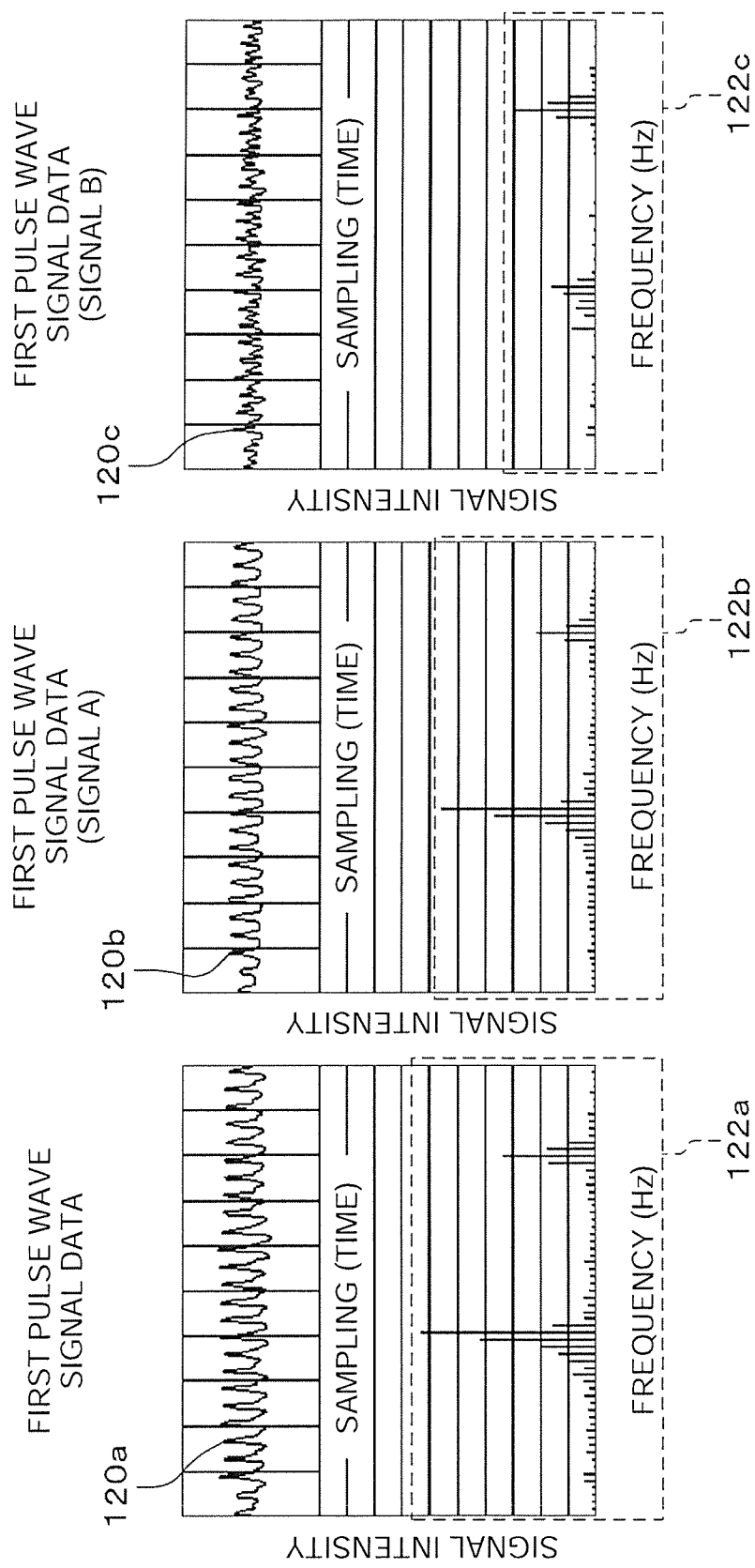

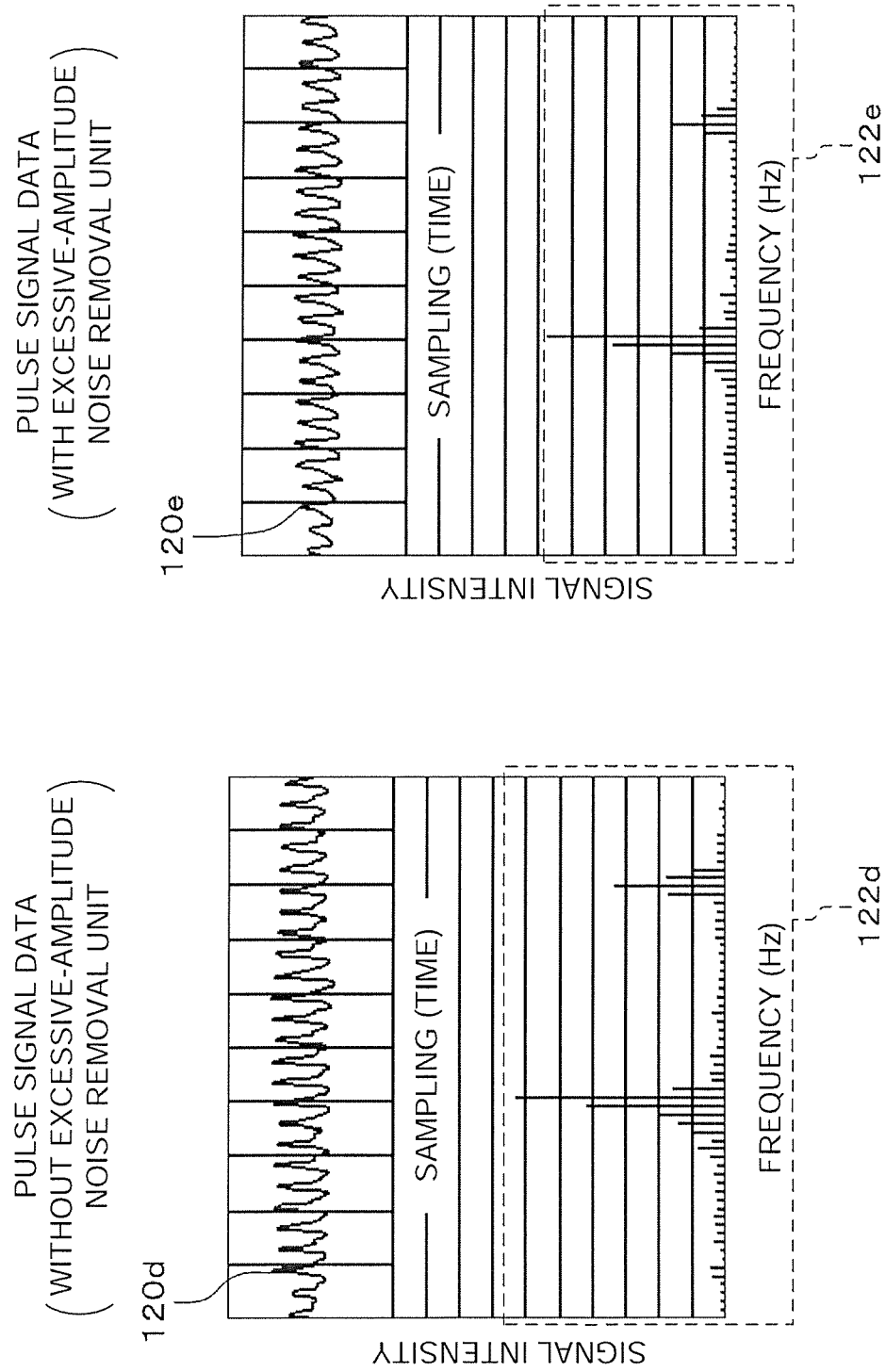

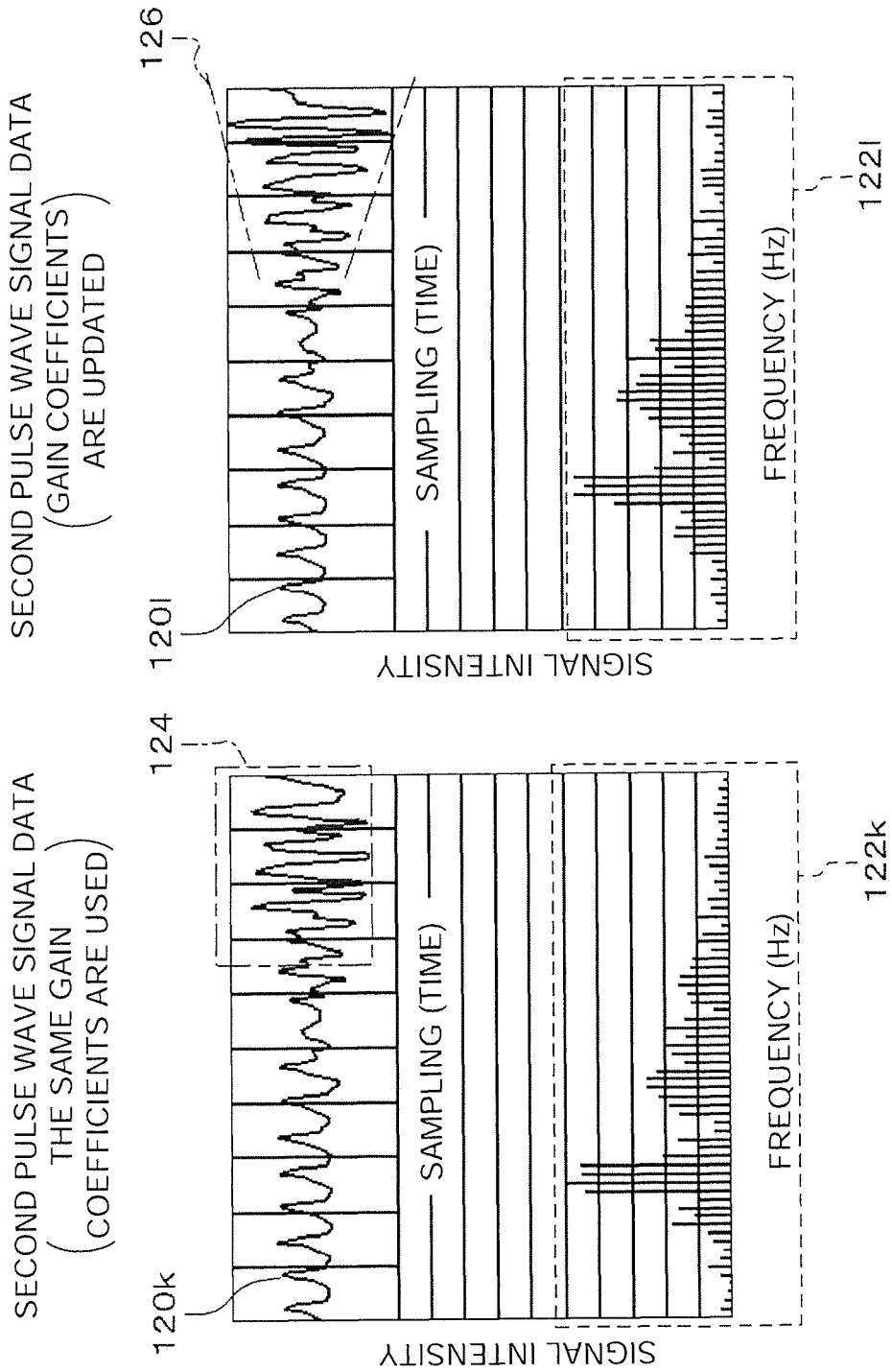

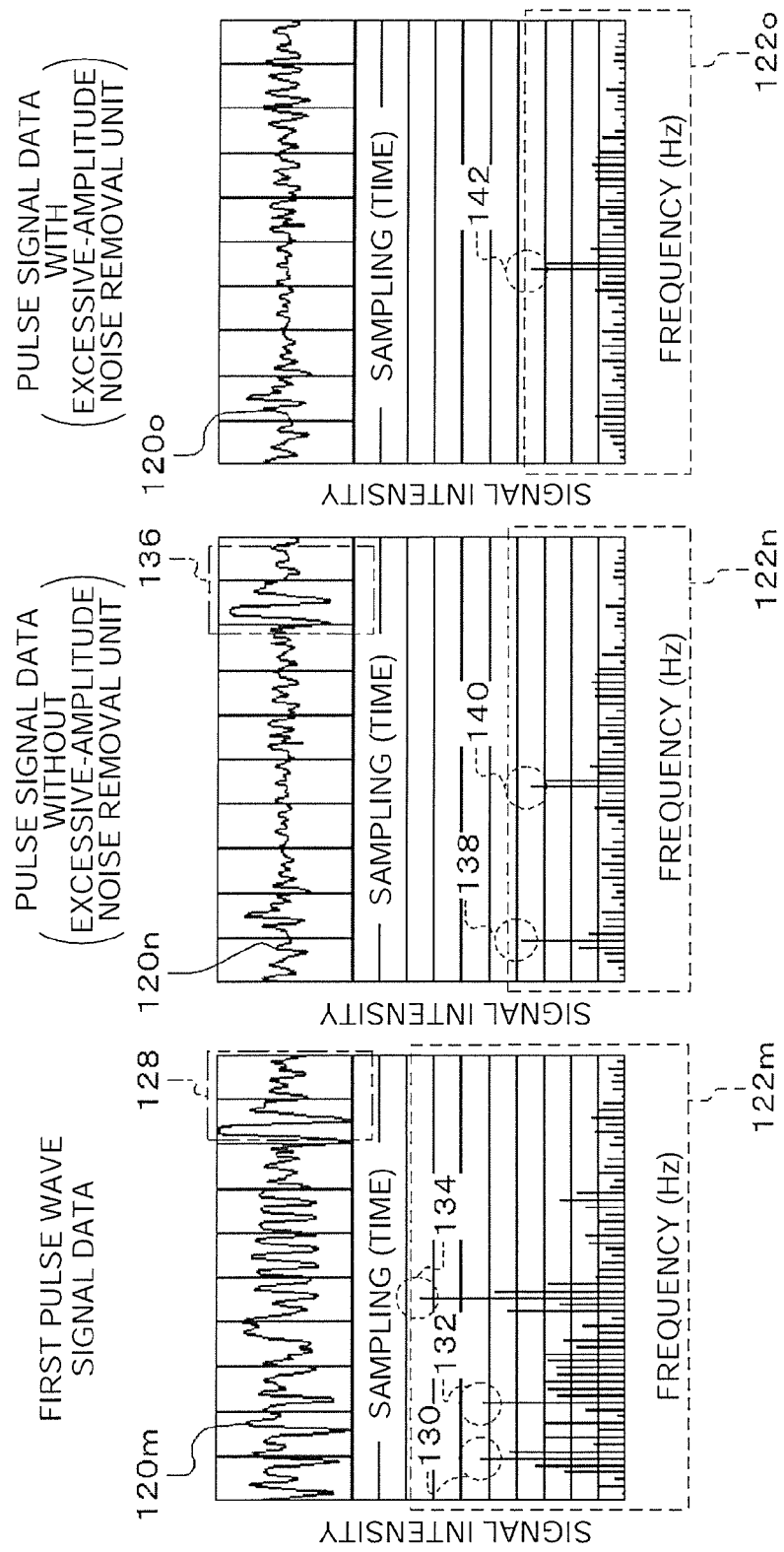

PULSE DETECTOR AND PULSE DETECTION METHOD

BACKGROUND

1. Technical Field

The present invention relates to a pulse detector and a pulse detection method.

2. Related Art

A pulse detector is a device for detecting the pulse originating from a human heartbeat. This device removes a noise signal component (motion affected signal) generated due to the effects of a motion of the human body from a signal (pulse wave signal) from a pulse wave sensor worn on an arm, a finger, or the like and detects only the signal (pulse signal) originating from a heartbeat.

In a pulse detector of a type in which an optical pulse wave sensor is worn on a finger, a wrist, or the like, since changes in the bloodstream can occur due to a motion of the finger or wrist itself or an impact near the finger or wrist, a noise signal can be input to the pulse wave sensor. This noise signal has higher signal level than a heartbeat component signal and is a great hindrance to the measurement (frequency analysis) of pulse. Such a noise should be removed as completely as possible. Particularly, in a pulse detector that measures the pulse continuously (every several seconds) in the course of daily activities and exercise, limitation to use under conditions where "the fingers may not be moved or touched" may greatly degrade its usability.

FIGS. 14A and 14B are graphs showing a noise signal in pulse wave signal data. Curves 120$p$ and 120$q$ on the top of each graph show the waveforms of pulse wave signal data, and bar graphs 122$p$ and 122$q$ on the bottom show the results of frequency analysis by fast-Fourier transform (FFT). FIG. 14A shows a state where a noise signal is not superimposed on pulse wave signal data, and FIG. 14B shows a state where noise signals 144 and 146 are superimposed on pulse wave signal data. A sensor output signal that cancels the heartbeat component is generated by an impact to the vicinity of the pulse wave sensor and a motion of a finger or the wrist. The low-frequency component of this large power signal may lead to an error in the pulse detection.

A sensor such as a pulse oximeter that optically acquires changes in blood volume is normally required to be worn at a location, such as the fleshy side of a finger, the palm, or a nail, where a large volume of arterial blood flow appears near the skin. Therefore, in many pulse detectors of the related art, a technique in which a pulse wave sensor is mounted at such a position as described above is proposed (for example, see JP-A-2005-198829). Moreover, when an external sensor and sensor cable are eliminated, and the sensor is embedded in a device body, the usability thereof increases.

Moreover, JP-A-2007-054471, for example, discloses a technique in which a pulse detector includes a plurality of band-pass filters and removes a noise component by subjecting signals obtained from a pulse wave sensor to filtering by a band-pass filter that passes a frequency signal near the frequency of the present pulse.

According to the technique disclosed in JP-A-2005-198829, the pulse wave sensor is worn on a finger, the palm, the wrist, or the like, particularly, where a motion occurs more frequently than other parts of the human body. Therefore, when a user wearing the sensor moves a portion near the hand, changes in the bloodstream occur different those in the bloodstream caused by a heartbeat as noise caused by a motion of the hand. The changes are input to a signal caught by the pulse wave sensor as noise. Thus, there is a case where the presence of this noise becomes a hindrance to analysis of pulse frequencies.

Moreover, when the user wearing the sensor touches the position in which the pulse wave sensor is worn or the peripheries thereof with an object or another part of the user's body, changes in the bloodstream occur differently from those in the bloodstream caused by a heartbeat as noise caused by a touch on the hand. Since the pulse wave sensor catches the changes in the bloodstream, the changes are input to a pulse wave sensor output signal as noise. Thus, there is a case where the presence of this noise becomes a hindrance to analysis of pulse frequencies.

The above-mentioned problems have a high degree of influence on a device in which the pulse wave sensor is embedded in a device body. The following can be thought of as the reasons thereof. Bones such as the radius and ulna, tendons, and muscles come together in the wrist, and changes in the bloodstream occur when the shapes of the tendons and muscles are greatly changed with the movement of a finger, the hand, and the wrist. Looking into the flow of arterial and venous blood, the arterial blood exhibits clearer changes in the bloodstream with a heartbeat than the venous blood, and accordingly, the rhythm of a heartbeat appears more clearly as a pulse wave sensor signal. The heartbeats are rarely detected in the venous bloodstream. However, since the subcutaneous tissue on the outer side of the wrist includes few arterial blood vessels (or they are located at a deeper side), changes in the bloodstream caused by external factors are more dominant than the changes in the bloodstream caused by the heartbeat when the bloodstream is caught by the pulse wave sensor. Therefore, it may be difficult to detect the changes in the bloodstream caused by the heartbeat when a motion of the hand or an impact to the peripheries of the hand is input to the sensor.

Moreover, according to the technique disclosed in JP-A-2007-054471, execution of such processing on a hardware circuit must involve many determination processes based on IF statements, which may increase the processing time and load. Therefore, the use of this technique in a pulse detector having a size as small as a wristwatch is not desirable from the perspectives of processing ability and consumption power.

SUMMARY

An advantage of some aspects of the invention is to solve at least a part of the problems mentioned above and the invention can be embodied as the following forms or application examples.

Application Example 1

According to this application example, there is provided a pulse detector that detects a pulse signal originating from the pulse of the human body, including: a pulse wave sensor that detects and outputs a first pulse wave signal in which the pulse signal and a noise signal are mixed; and a first filtering unit that generates an adaptive spectral line enhancer based on the first pulse wave signal, divides the first pulse wave signal into a first signal and a second signal, and outputs a second pulse wave signal including at least the first signal.

The first pulse wave signal obtained from the pulse wave sensor is divided into a signal component (first signal) having autocorrelation and the other components (second signal) using the first pulse wave signal itself as a reference signal, and pulse frequency analysis is performed based on the first signal. Specifically, the first pulse wave signal is passed through the adaptive spectral line enhancer which is one kind of adaptive filter, whereby the first pulse wave signal is divided into a heartbeat component and a normal signal component which are the first signal having autocorrelation and which contains changes in blood volume caused by swinging of the arm during walking or jogging, and an abnormal unexpected signal component which is the second signal having no autocorrelation and which contains changes in the bloodstream caused by a motion of a finger or the wrist and changes in the bloodstream caused by a touch on a finger or the wrist.

According to this configuration, since an impact noise signal having a high signal level is decreased in the first signal, it is possible to decrease the possibility of an error or failure in the pulse detection when specifying the frequency component representing the pulse at the time of performing the pulse frequency analysis. Moreover, since the pulse wave frequency analysis is performed after the first pulse wave signal obtained from the pulse wave sensor is divided into the signal component having autocorrelation and the other components, it is possible to alleviate the influence of an unexpected noise signal.

Application Example 2

According to this application example, in the pulse detector of the above-mentioned application example, the first filtering unit may include a combining unit that calculates the sum of the first and second signals by applying first gain coefficients to change a ratio thereof to generate the second pulse wave signal and outputs the second pulse wave signal.

The pulse detection is performed based on a signal which is the sum of the first and second signals with a ratio thereof changed. Specifically, (Output Signal)=(h1×Signal A)+(h2×Signal B) (where, gain coefficients are h1≥1.0 and h2<1.0).

According to this configuration, it is possible to alleviate the influence of an impact and increase the ability to track abrupt changes in the pulse component and motion component. For example, when a person whose resting pulse rate is 60 starts fast-pace jogging and his/her pulse rate abruptly increases to 150, if the tracking ability of an adaptive filter is slower than the rise of pulse rate, there is a possibility that the adaptive filter may reject a heartbeat component signal that is rising abruptly. However, this configuration is able to eliminate such a possibility.

Application Example 3

According to this application example, in the pulse detector of the above-mentioned application example, the first filtering unit may include: a detection unit that detects whether or not a change in the pulse wave has increased over a predetermined threshold based on the first pulse wave signal; and a switching unit that switches the first gain coefficients to second gain coefficients in accordance with an output signal of the detection unit.

The amplitudes of signals output from the pulse wave sensor are monitored, and when a signal whose amplitude is equal to or larger than a predetermined amplitude is input, the gain coefficients are changed so that a weighting is applied to the first signal. Specifically, the coefficients are h1=1.0 and h2=0.5 in a normal mode and are h1=1.2 and h2=0.0 in an impact mode.

According to this configuration, in the impact mode, resistance to an impact signal is increased (that is, it becomes easy to specify the frequency of pulse waves). Moreover, in the normal mode, a state where abrupt changes in the pulse and motion can be dealt with easily can be maintained while providing a certain degree of impact resistance.

Application Example 4

According to this application example, in the pulse detector of the above-mentioned application example, when the detection unit has detected that the change in the pulse wave has increased over the predetermined threshold, the first filtering unit may not perform a process of updating the filters of the adaptive spectral line enhancer.

According to this configuration, in the impact mode, resistance to an impact signal is increased (that is, it becomes easy to specify the frequency of pulse waves). Moreover, in the normal mode, a state where abrupt changes in the pulse and motion can be dealt with easily can be maintained while providing a certain degree of impact resistance.

Application Example 5

According to this application example, in the pulse detector of above-mentioned application example, when the detection unit is unable to detect for a predetermined period that the change in the pulse wave has increased over the predetermined threshold based on the first pulse wave signal, the switching unit may switch the second gain coefficients to the first gain coefficients.

When the signal output from the pulse wave sensor has not increased over a threshold signal amplitude for a predetermined period after the gain coefficients were changed, the gain coefficients are switched to the original coefficients.

According to this configuration, in the impact mode, resistance to an impact signal is increased (that is, it becomes easy to specify the frequency of pulse waves). Moreover, in the normal mode, a state where abrupt changes in the pulse and motion can be dealt with easily can be maintained while providing a certain degree of impact resistance.

Application Example 6

According to a sixth application example, in the pulse detector of the above-mentioned application example, the pulse detector may further include: a motion sensor that detects and outputs a motion signal in response to a motion of the human body; and a second filtering unit that generates an adaptive filter based on the motion signal to extract a noise signal in the second pulse wave signal and outputs the pulse signal in which the noise signal is removed from the second pulse wave signal.

The amplitudes of signals output from the pulse wave sensor are monitored, and when a signal whose amplitude is equal to or larger than a predetermined amplitude is input, the filtering is performed without updating the filter coefficients of the adaptive filter.

According to this configuration, the coefficients of the adaptive filter that constructs the adaptive spectral line enhancer are not updated (in the impact mode) with the first pulse wave signal used as a reference signal, in which a noise signal is mixed. By doing so, the adaptive filter itself will not (rarely) allow passage of an impact noise signal. Therefore, it is possible to maintain a state where the pulse is detected more easily as compared to the case of an adaptive filter that is configured such that the filter coefficients are always updated.

Application Example 7

According to this application example, in the pulse detector of the above-mentioned application example, the first signal may include a heartbeat signal component and a normal signal component which contains changes in the bloodstream caused by a swinging motion of the arm during walking or jogging, and the second signal may include an abnormal unexpected signal component which contains changes in the bloodstream caused by a motion of a finger or the wrist and changes in the bloodstream caused by a touch on a finger or the wrist.

According to this configuration, since an impact noise signal having a high signal level is decreased in the first signal, it is possible to decrease the possibilities of an error or failure in the pulse detection when specifying the frequency component representing the pulse at the time of performing the pulse frequency analysis.

Application Example 8

According to this application example, there is provided a pulse detector that detects a pulse signal originating from the pulse of the human body, including: a pulse wave sensor that detects and outputs a first pulse wave signal in which the pulse signal and a noise signal are mixed; a motion sensor that detects and outputs a motion signal in response to a motion of the human body; a first filtering unit that generates an adaptive filter based on a third pulse wave signal, divides the first pulse wave signal into a first signal and a second signal, and outputs a second pulse wave signal including at least the first signal; and a second filtering unit that generates an adaptive filter based on the motion signal to extract the noise signal in the second pulse wave signal and outputs the third pulse wave signal in which the noise signal is removed from the second pulse wave signal, wherein the third pulse wave signal is detected as the pulse signal.

The adaptive spectral line enhancer calculates adaptive filter coefficients using a signal, which has passed through the motion-affected component filtering unit, as a reference signal. By doing so, the first pulse wave signal is divided into a solely heartbeat signal component which is the first signal having autocorrelation, an abnormal unexpected signal component which is the second signal having no autocorrelation and which contains changes in the bloodstream caused by a motion of a finger or the wrist and changes in the bloodstream caused by a touch on a finger or the wrist, and a normal signal component which is also the second signal and which contains changes in the bloodstream caused by swinging of the arm during walking or jogging.

According to this configuration, the pulse wave frequency analysis is performed more easily.

Application Example 9

According to this application example, in the pulse detector of the above-mentioned application example, the first signal may include a heartbeat signal component, and the second signal may include an abnormal unexpected signal component which contains changes in the bloodstream caused by a motion of a finger or the wrist and changes in the bloodstream caused by a touch on a finger or the wrist and a normal signal component which contains changes in the bloodstream caused by a swinging motion of the arm during walking or jogging.

According to this configuration, since an impact noise signal having a high signal level is decreased in the first signal, it is possible to decrease the possibilities of an error or failure in the pulse detection when specifying the frequency component representing the pulse at the time of performing the pulse frequency analysis.

Application Example 10

According to this application example, there is provided a pulse detection method for causing a computer to detect a pulse signal originating from the pulse of the human body, the computer including a pulse wave sensor that detects a first pulse wave signal in which the pulse signal and a noise signal are mixed, the method including: first filtering which involves generating an adaptive spectral line enhancer based on the first pulse wave signal, dividing the first pulse wave signal into a first signal and a second signal, and outputting a second pulse wave signal including at least the first signal.

The first pulse wave signal obtained from the pulse wave sensor is divided into a first signal having autocorrelation and a second signal, which is the remaining signal, using the first pulse wave signal itself as a reference signal, and pulse frequency analysis is performed based on the first signal. Specifically, the first pulse wave signal is passed through the adaptive spectral line enhancer which is one kind of adaptive filter, whereby the first pulse wave signal is divided into a normal signal component which is the first signal having autocorrelation and which contains a heartbeat component and changes in blood volume caused by swinging of the arm during walking or jogging, and an abnormal unexpected signal component which is the second signal having no autocorrelation and which contains changes in the bloodstream caused by a motion of a finger or the wrist and changes in the bloodstream caused by a touch on a finger or the wrist.

According to this configuration, since an impact noise signal having a high signal level is decreased in the first signal, it is possible to decrease the possibilities of an error or failure in the pulse detection when specifying the frequency component representing the pulse at the time of performing the pulse frequency analysis. Moreover, since the pulse wave frequency analysis is performed after the first pulse wave signal obtained from the pulse wave sensor is divided into the signal component having autocorrelation and the other components, it is possible to alleviate the influence of an unexpected noise signal.

Application Example 11

According to this application example, in the pulse detection method of the above-mentioned application example, the first filtering step may include calculating the sum of the first and second signals by applying first gain coefficients to change a ratio thereof to generate the second pulse wave signal and outputting the second pulse wave signal.

The pulse detection is performed based on a signal which is the sum of the first and second signals with a ratio thereof changed. Specifically, (Output Signal)=(h1×Signal A)+(h2×Signal B) (where, gain coefficients are h1≥1.0 and h2<1.0).

According to this configuration, it is possible to alleviate the influence of an impact and increase the ability to track abrupt changes in the pulse component and motion component. For example, when a person whose resting pulse rate is 60 starts fast-pace jogging and his/her pulse rate abruptly increases to 150, if the tracking ability of an adaptive filter is slower than the rise of pulse rate, there is a possibility that the adaptive filter may reject heartbeat component signal that is rising abruptly. However, this configuration is able to eliminate such a possibility.

Application Example 12

According to this application example, in the pulse detection method of the above-mentioned application example, the first filtering step may include: detecting whether or not a change in the pulse wave has increased over a predetermined threshold based on the first pulse wave signal; and switching the first gain coefficients to second gain coefficients in accordance with an output signal obtained in the detecting.

The amplitudes of signals output from the pulse wave sensor are monitored, and when a signal whose amplitude is equal to or larger than a predetermined amplitude is input, the gain coefficients are changed so that a weighting is applied to the first signal. Specifically, the coefficients are h1=1.0 and h2=0.5 in a normal mode and are h1=1.2 and h2=0.0 in an impact mode.

According to this configuration, in the impact mode, resistance to an impact signal is increased (that is, it becomes easy to specify the frequency of pulse waves). Moreover, in the normal mode, a state where abrupt changes in the pulse and motion can be dealt with easily can be maintained while providing a certain degree of impact resistance.

Application Example 13

According to this application example, in the pulse detection method of the above-mentioned application example, when it is detected in the detection step that the change in the pulse wave has increased over the predetermined threshold, a process of updating the filters of the adaptive spectral line enhancer may be not performed in the first filtering step.

According to this configuration, in the impact mode, resistance to an impact signal is increased (that is, it becomes easy to specify the frequency of pulse waves). Moreover, in the normal mode, a state where abrupt changes in the pulse and motion can be dealt with easily can be maintained while providing a certain degree of impact resistance.

Application Example 14

According to this application example, in the pulse detection method of the above-mentioned application example, when in the detection step, it was unable to detect for a predetermined period that the change in the pulse wave has increased over the predetermined threshold based on the first pulse wave signal, the second gain coefficients may be switched to the first gain coefficients in the switching step.

When the signal output from the pulse wave sensor has not increased over a threshold signal amplitude for a predetermined period after the gain coefficients were changed, the gain coefficients are switched to the original coefficients.

According to this configuration, in the impact mode, resistance to an impact signal is increased (that is, it becomes easy to specify the frequency of pulse waves). Moreover, in the normal mode, a state where abrupt changes in the pulse and motion can be dealt with easily can be maintained while providing a certain degree of impact resistance.

Application Example 15

According to this application example, in the pulse detection method of the above-mentioned application example, the computer may include a motion sensor that detects and outputs a motion signal in response to a motion of the human body; and the method may include second filtering which involves generating an adaptive filter based on the motion signal to extract a noise signal in the second pulse wave signal and outputting the pulse signal in which the noise signal is removed from the second pulse wave signal.

The amplitudes of signals output from the pulse wave sensor are monitored, and when a signal whose amplitude is equal to or larger than a predetermined amplitude is input, the filtering is performed without updating the filter coefficients of the adaptive filter.

According to this configuration, the coefficients of the adaptive filter that constructs the adaptive spectral line enhancer are not updated (in the impact mode) with the first pulse wave signal used as a reference signal, in which a noise signal is mixed. By doing so, the adaptive filter itself will not (rarely) allow passage of an impact noise signal. Therefore, it is possible to maintain a state where the pulse is detected more easily as compared to the case of an adaptive filter that is configured such that the filter coefficients are always updated.

Application Example 16

According to this application example, in the pulse detection method of the above-mentioned application example, the first signal may include a heartbeat signal component and a normal signal component which contains changes in the bloodstream caused by a swinging motion of the arm during walking or jogging, and the second signal may include an abnormal unexpected signal component which contains changes in the bloodstream caused by a motion of a finger or the wrist and changes in the bloodstream caused by a touch on a finger or the wrist.

According to this configuration, since an impact noise signal having a high signal level is decreased in the first signal, it is possible to decrease the possibilities of an error or failure in the pulse detection when specifying the frequency component representing the pulse at the time of performing the pulse frequency analysis.

Application Example 17

According to this application example, there is provided a pulse detection method for causing a computer to detect a pulse signal originating from the pulse of the human body, the computer including a pulse wave sensor that detects a first pulse wave signal in which the pulse signal and a noise signal are mixed and a motion sensor that detects and outputs a motion signal in response to a motion of the human body, the method including: first filtering which involves generating an adaptive filter based on a third pulse wave signal, dividing the first pulse wave signal into a first signal and a second signal, and outputting a second pulse wave signal including at least the first signal; and second filtering which involves generating an adaptive filter based on the motion signal to extract the noise signal in the second pulse wave signal and outputting the third pulse wave signal in which the noise signal is removed from the second pulse wave signal, wherein the third pulse wave signal is detected as the pulse signal.

The adaptive spectral line enhancer calculates adaptive filter coefficients using a signal, which has passed through the motion-affected component filtering unit, as a reference signal being the third pulse wave signal. By doing so, the third pulse wave signal is divided into a solely heartbeat component which is the first signal having autocorrelation, an abnormal unexpected signal component which is the second signal having no autocorrelation and which contains changes in the bloodstream caused by a motion of a finger or the wrist and changes in the bloodstream caused by a touch on a finger or the wrist, a normal change in bloodstream signal component which is also the second signal and which contains changes in the bloodstream caused by swinging of the arm during walking or jogging.

According to this configuration, the pulse wave frequency analysis is performed more easily.

Application Example 18

According to this application example, in the pulse detection method of the above-mentioned application example, the first signal may include a heartbeat signal component, and the second signal may include an abnormal unexpected signal component which contains changes in the bloodstream caused by a motion of a finger or the wrist and changes in the bloodstream caused by a touch on a finger or the wrist and a normal signal component which contains changes in the bloodstream caused by a swinging motion of the arm during walking or jogging.

According to this configuration, since an impact noise signal having a high signal level is decreased in the first signal, it is possible to decrease the possibilities of an error or failure in the pulse detection when specifying the frequency component representing the pulse at the time of performing the pulse frequency analysis.

BRIEF DESCRIPTION OF THE DRAWINGS

The invention will be described with reference to the accompanying drawings, wherein like numbers reference like elements.

FIGS. 7A to 7C are diagrams showing normal-mode output data from the pulse wave sensor of the pulse detector according to the first embodiment, in which FIG. 7A shows first pulse wave signal data, FIG. 7B shows first pulse wave signal data (signal A), and FIG. 7C shows first pulse wave signal data (signal B).

FIG. 8A shows pulse signal data when an excessive-amplitude noise removal unit is not used, and FIG. 8B shows pulse signal data when the excessive-amplitude noise removal unit of the pulse detector according to the first embodiment is used.

FIGS. 9A to 9C are diagrams showing impact-mode output data from the pulse wave sensor of the pulse detector according to the first embodiment, in which FIG. 9A shows first pulse wave signal data, FIG. 9B shows first pulse wave signal data (signal A), and FIG. 9C shows first pulse wave signal data (signal B).

FIG. 11A shows second pulse wave signal data when the same gain coefficients are used in the normal mode and the impact mode, and FIG. 11B shows second pulse wave signal data when the coefficients of an adaptive filter are updated even after the impact mode has started.

FIG. 13A shows first pulse wave signal data output from a pulse wave sensor of a pulse detector according to the second embodiment, FIG. 13B shows pulse signal data when an excessive-amplitude noise removal unit is not used, and FIG. 13C shows pulse signal data when the excessive-amplitude noise removal unit of the pulse detector according to the second embodiment is used.

DESCRIPTION OF EXEMPLARY EMBODIMENTS

Hereinafter, embodiments of the invention will be described with reference to the accompanying drawings.

First Embodiment

Figure 1:
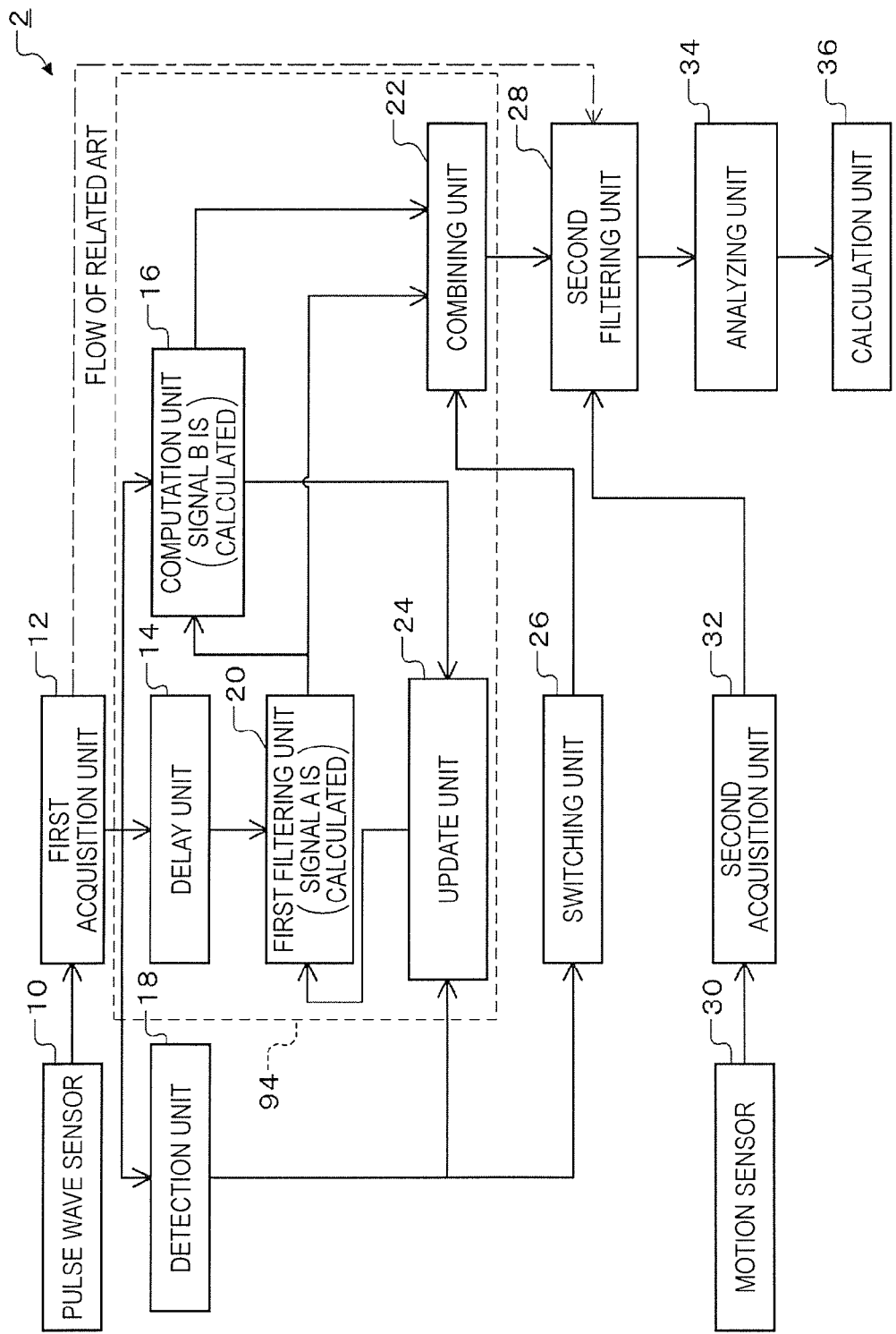
FIG. 1 is a functional block diagram of a pulse detector according to a first embodiment.
Figure 2:
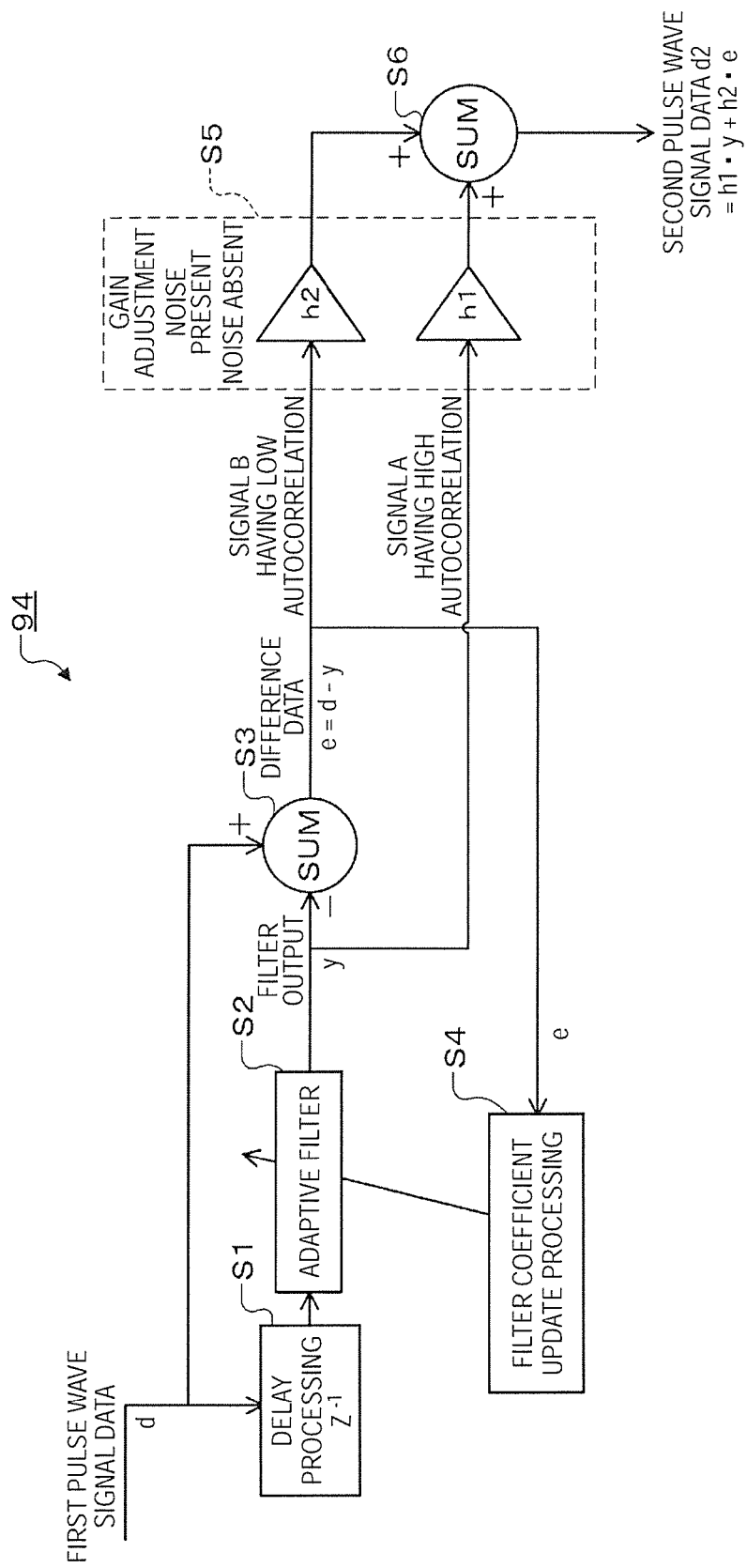
FIG. 2 is a block diagram of processing steps in an excessive-amplitude noise removal unit according to the first embodiment.

FIG. 1 is a functional block diagram of a pulse detector 2 according to the first embodiment. FIG. 2 is a block diagram of processing steps in a noise removal unit (adaptive spectral line enhancer) 94 according to the first embodiment.

A pulse wave sensor 10 of the pulse detector 2 according to the present embodiment detects a first pulse wave signal of a subject. The first pulse wave signal is subjected to amplification, AD conversion, and sampling in a first acquisition unit 12 and is then stored in a buffer. In the present embodiment, the sampling frequency is "16 Hz."

The first pulse wave signal is the sum of an original pulse component and a motion component based on a body motion. The first pulse wave signal stored in the buffer is output to a delay unit 14, a computation unit 16, and a detection unit 18.

The delay unit 14 delays the first pulse wave signal and outputs the signal to an first filtering unit 20.

The first filtering unit 20 applies an autocorrelation filter whose filter coefficient is multiplied to the delayed first pulse wave signal to calculate a signal A (first signal) and outputs the signal A to the computation unit 16 and a combining unit 22.

The computation unit 16 subtracts the signal A obtained through the autocorrelation filter from the first pulse wave signal to calculate a signal B (second signal) and outputs the calculated difference data to an update unit 24 and the combining unit 22.

The signal A includes a heartbeat signal component and a normal signal component which contains changes in the bloodstream caused by a swinging motion of the arm during walking or jogging. The signal B includes an abnormal unexpected signal component which contains changes in the bloodstream caused by a motion of a finger or the wrist and changes in the bloodstream caused by a touch on a finger or the wrist.

In the present embodiment, since an impact noise signal having a high signal level is decreased in the signal A, it is possible to decrease the possibilities of an error or failure in the pulse detection when specifying the frequency component representing the pulse at the time of performing the pulse frequency analysis.

The detection unit 18 detects a state where the pulse wave signal is increased too high and outputs the detection results to the update unit 24 and a switching unit 26.

The update unit 24 appropriately calculates a constant in accordance with the difference data input from the computation unit 16 and outputs the calculated constant to the autocorrelation filter as the filter coefficient. Moreover, even when the pulse wave signal is increased too much, the update unit 24 updates the filter coefficient and outputs the updated filter coefficient to the autocorrelation filter.

The switching unit 26 forcibly sets a gain coefficient of the combining unit 22 to a predetermined value (a first or second gain coefficient). If a signal output from the pulse wave sensor 10 has not increased over a threshold signal amplitude for a predetermined period after the gain coefficient was changed, the gain coefficient is changed to the original gain coefficient.

In the present embodiment, in an impact mode, resistance to an impact signal is increased (that is, it becomes easy to specify the frequency of pulse waves). Moreover, in a normal mode, a state where abrupt changes in the pulse and motion can be dealt with easily can be maintained while providing a certain degree of impact resistance.

The combining unit 22 performs signal combining processing using the signals A and B and the gain coefficient and outputs second pulse wave signal data to a second filtering unit 28. Moreover, the combining unit 22 performs motion detection processing based on a signal which is the sum of the signals A and B with a ratio thereof changed. Specifically, (Output Signal)=(h1×Signal A)+(h2×Signal B) (where, gain coefficients are h1≥1.0 and h2<1.0).

In the present embodiment, it is possible to alleviate the influence of an impact and increase the ability to track abrupt changes in the pulse component and motion component. For example, when a person whose resting pulse rate is 60 starts fast-pace jogging and his/her pulse rate abruptly increases to 150, if the tracking ability of an adaptive filter is slower than the rise of pulse rate, there is a possibility that the adaptive filter may reject heartbeat component signal that is rising abruptly. However, this configuration is able to eliminate such a possibility.

A motion sensor 30 is configured by an acceleration sensor or the like and measures a motion signal of the subject. The motion signal is subjected to amplification, AD conversion, and sampling in a second acquisition unit 32 and is then stored in a buffer. The motion signal stored in the buffer is output to the second filtering unit 28.

The second filtering unit 28 includes an adaptive filter, a subtractor, and a coefficient calculator which are not shown. The adaptive filter is configured by an FIR filter and calculates an estimated value of the body motion component. The subtractor subtracts the estimated value from the second pulse wave signal. The coefficient calculator sequentially calculates a constant in accordance with a difference signal, and the calculated constant is set to the adaptive filter.

In the present embodiment, the coefficients of the adaptive filter that constructs the noise removal unit 94 are not updated in the impact mode with the first pulse wave signal used as a reference signal, in which a noise signal is mixed. By doing so, the adaptive filter itself will not (rarely) allow passage of an impact noise signal. Therefore, it is possible to maintain a state where the pulse is detected more easily as compared to the case of an adaptive filter that is configured such that the filter coefficients are always updated.

An analyzing unit 34 subjects a series of pulse signals to FFT processing to obtain the frequency components thereof. Among these frequency components, a component having the highest level is extracted as a pulse wave component.

A calculation unit 36 calculates a pulse rate which is the number of beats per minute based on the frequency of the pulse wave component. Thereafter, the calculation unit 36 displays the calculated pulse rate on a display unit (not shown).

The noise removal unit 94 includes the delay unit 14, the computation unit 16, the first filtering unit 20, the update unit 24, and the combining unit 22.

The noise removal unit 94, the detection unit 18, and the switching unit 26 constitute a first filtering unit.

Next, the noise removal unit 94 according to the present embodiment will be described for each processing step with reference to FIG. 2.

First, first pulse wave signal data d which are obtained by sampling the first pulse wave signal detected by the pulse wave sensor 10 include a pulse signal component which is a desired signal to be detected and a noise component associated to a body motion. Here, the delay unit 14 delays the first pulse wave signal data d which are based on the first pulse wave signal from the pulse wave sensor 10 (step S1). The first filtering unit 20 applies an autocorrelation filter whose filter coefficient is multiplied to the delayed first pulse wave signal data d to obtain a filter output y (step S2). The computation unit 16 subtracts the filter output y from the first pulse wave signal data d (step S3) to calculate difference data e as the signal B having no autocorrelation. Moreover, the difference data e are output to the update unit 24. The update unit 24 appropriately calculates a constant in accordance with the difference data e (step S4), and the calculated constant is set to the autocorrelation filter. Moreover, the filter output y is used as the signal A having autocorrelation.

The gain coefficients of the signals A and B obtained in this way are adjusted (step S5), and the adjusted signals A and B are subjected to signal combining processing (step S6), whereby a pulse wave signal is extracted and used as second pulse wave signal data d2.

Hereinafter, the signal obtained by applying an adaptive filter whose filter coefficient is multiplied to the motion signal data which are obtained by sampling the motion signal from the motion sensor 30 will be referred to as a motion affected signal, namely an estimate of noise. The difference data obtained by subtracting the motion affected signal from the second pulse wave signal data d2 are used as the pulse signal.

In the following description, several embodiments will be described in accordance with a method of detecting changes in pulse waves and a processing order until the pulse is detected, or a method of setting an adaptive filter.

Figure 3:
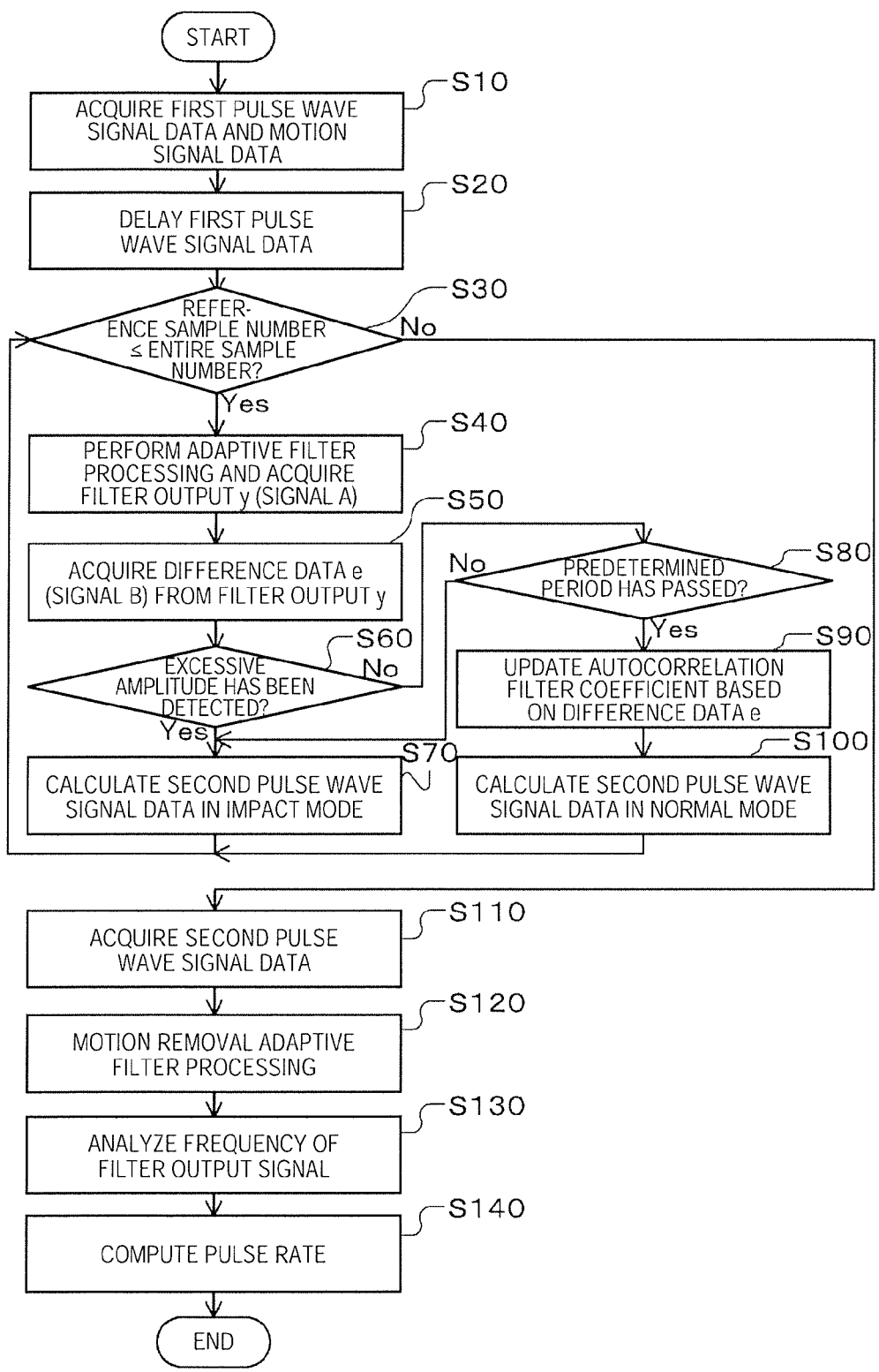
FIG. 3 is a flowchart of a pulse detection method in the pulse detector according to the first embodiment.

FIG. 3 is a flowchart of a pulse detection method in the pulse detector 2 according to the present embodiment. The flowchart shows the flow of processing in a first filtering step (steps S20 to S110) which is performed by an MPU 38 (see FIG. 6) in accordance with a pulse detection algorithm of the present embodiment. The first filtering step involves processing the second pulse wave signal data d2 and the motion signal data to extract the pulse signal, and ultimately, displaying and outputting the pulse rate on a liquid crystal display 42 (see FIG. 6) based on the pulse signal.

First, when a subject wearing the pulse detector 2 presses a predetermined button to start measurement with the pulse detector, the MPU 38 acquires and records the first pulse wave signal data d and the motion signal data into a RAM 40 (see FIG. 6) (step S10).

Subsequently, the first pulse wave signal data d are subjected to delay processing (step S20).

After that, the size relationship between a reference sample number and an entire sample number is determined (step S30). When the reference sample number is equal to or smaller than the entire sample number, the flow proceeds to step S40. When the reference sample number is larger than the entire sample number, the flow proceeds to step S110.

Subsequently, when the reference sample number is smaller than or equal to the entire sample number, the first pulse wave signal data d are passed to an autocorrelation filter, whereby the MPU 38 acquires and records the filter output y (signal A) into the RAM 40 (step S40).

After that, the MPU 38 acquires and records the difference data e, which are the difference between the first pulse wave signal data d and the filter output y, into the RAM 40 (step S50).

Subsequently, a determination is made as to whether or not a signal having an excessive amplitude is detected (step S60). When a signal having an excessive amplitude is detected, the flow proceeds to step S70. When a signal having an excessive amplitude is not detected, the flow proceeds to step S80.

After that, when a signal having an excessive amplitude is detected, the second gain coefficient in the impact mode is selected and the second pulse wave signal data d2 are calculated (step S70).

Subsequently, the flow returns to step S30.

On the other hand, when a signal having an excessive amplitude is not detected, it is determined whether or not a predetermined period has passed (step S80). When the predetermined period has passed, the flow proceeds to step S90. When the predetermined period has not passed, the flow proceeds to step S70.

After that, when the predetermined period has passed, the autocorrelation filter coefficients are updated based on the difference data e (step S90).

Subsequently, the first gain coefficient in the normal mode is selected and the second pulse wave signal data d2 are calculated (step S100).

After that, the flow returns to step S30.

On the other hand, when the reference sample number is larger than the entire sample number, the MPU 38 acquires and records the second pulse wave signal data d2 into the RAM 40 (step S110). The MPU 38 subjects the second pulse wave signal data d2 to adaptive filtering for removing a body motion component and acquires and records the pulse signal data into the RAM 40 (step S120). The MPU 38 subjects the pulse signal data to FFT processing to specify the frequency representing the pulse (step S130) and calculates the pulse rate from the frequency (step S140). The calculated pulse rate is displayed and output to the liquid crystal device 42 (see FIG. 6). The series of above-described processing (steps S10 to S140) are continued until the subject inputs a measurement stop instruction to the pulse detector 2.

Two Signal Processing Modes

The normal mode is used when there is no impact or the like, and the original pulse can be measured stably, and in this mode, a slightly higher weight is applied to the signal A, and a slightly lower weight is applied to the signal B. During this mode, the process of updating the filter coefficients that construct the noise removal unit 94 is performed for each target tap (sampling). The first gain coefficient, for example, is used as the gain coefficient in this mode.

The impact mode is used when an impact signal different from the component obtained when the pulse can be measured stably is mixed into the output signal of the pulse wave sensor 10, and in this mode, the weight applied to the signal A is increased, and the weight applied to the signal B is set to 0. This mode lasts for a predetermined period after an impact is detected. When no impact is detected for a predetermined period, the processing mode returns to the normal mode. During this mode, the process of updating the filter coefficients that construct the noise removal unit 94 is not performed. The second gain coefficient, for example, is used as the gain coefficient in this mode.

Figure 4A:
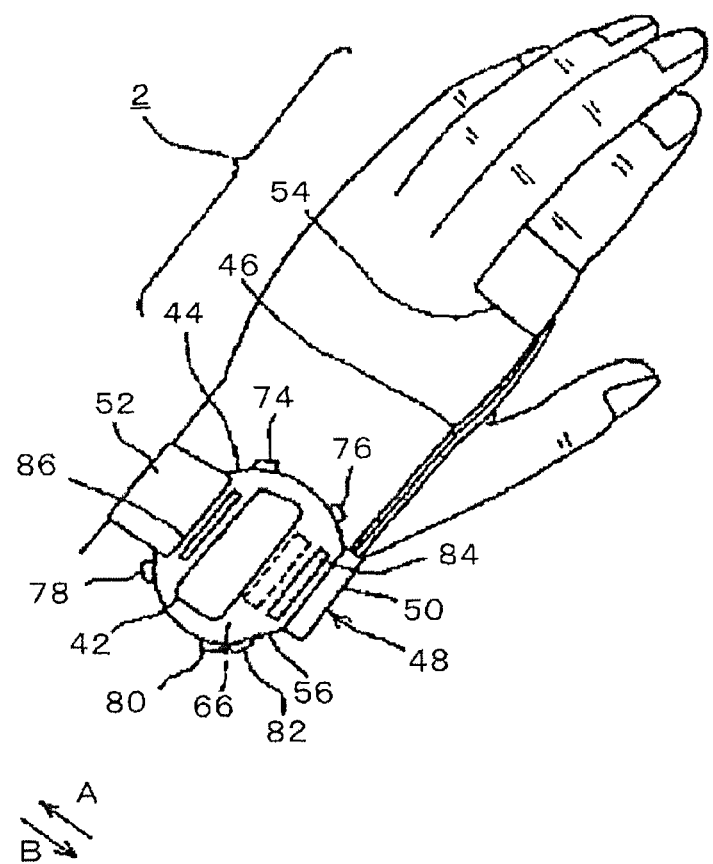
FIG. 4A is a diagram illustrating a configuration of the pulse detector according to the first embodiment.

FIG. 4A is a diagram illustrating a configuration of the pulse detector 2 according to this embodiment. The pulse detector 2 is roughly configured to include a main body 44 that has a wristwatch-like structure, a cable 46 connected to the main body 44, and the pulse wave sensor 10 provided at the distal end of the cable 46.

A connector piece 48 is provided at one end of the cable 46. The connector piece 48 is detachably attached to a connector unit 50 that is provided on the 6 o'clock side of the main body 44.

The main body 44 includes a wrist band 52 that is wound around a wrist from the 12 o'clock side of a wristwatch and fixed at the 6 o'clock side. With this wrist band 52, the main body 44 is detachably worn around the wrist.

Figure 4B:
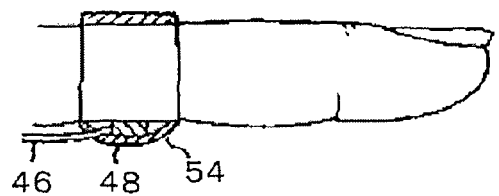
FIG. 4B is a side view of a pulse wave sensor of the pulse detector according to the first embodiment.

FIG. 4B is a side view near the pulse wave sensor 10 of the pulse detector 2 according to the present embodiment. The pulse wave sensor 10 is attached to a portion an index finger ranging from the root to the finger joint in a state of being shielded by a sensor fixing band 54. In this way, by attaching the pulse wave sensor 10 to the base of the finger, the length of the cable 46 can be reduced, and the cable 46 may not cause problems during running. Moreover, when the distribution of the body temperature is measured at positions ranging from the palm to the finger tip, the temperature at the finger tip may decrease greatly on cold days whereas the temperature at the base of the finger may decrease a relatively small amount. Therefore, by attaching the pulse wave sensor 10 to the base of the finger, the pulse rate or the like can be measured accurately while running outdoors on cold days.

Figure 5:
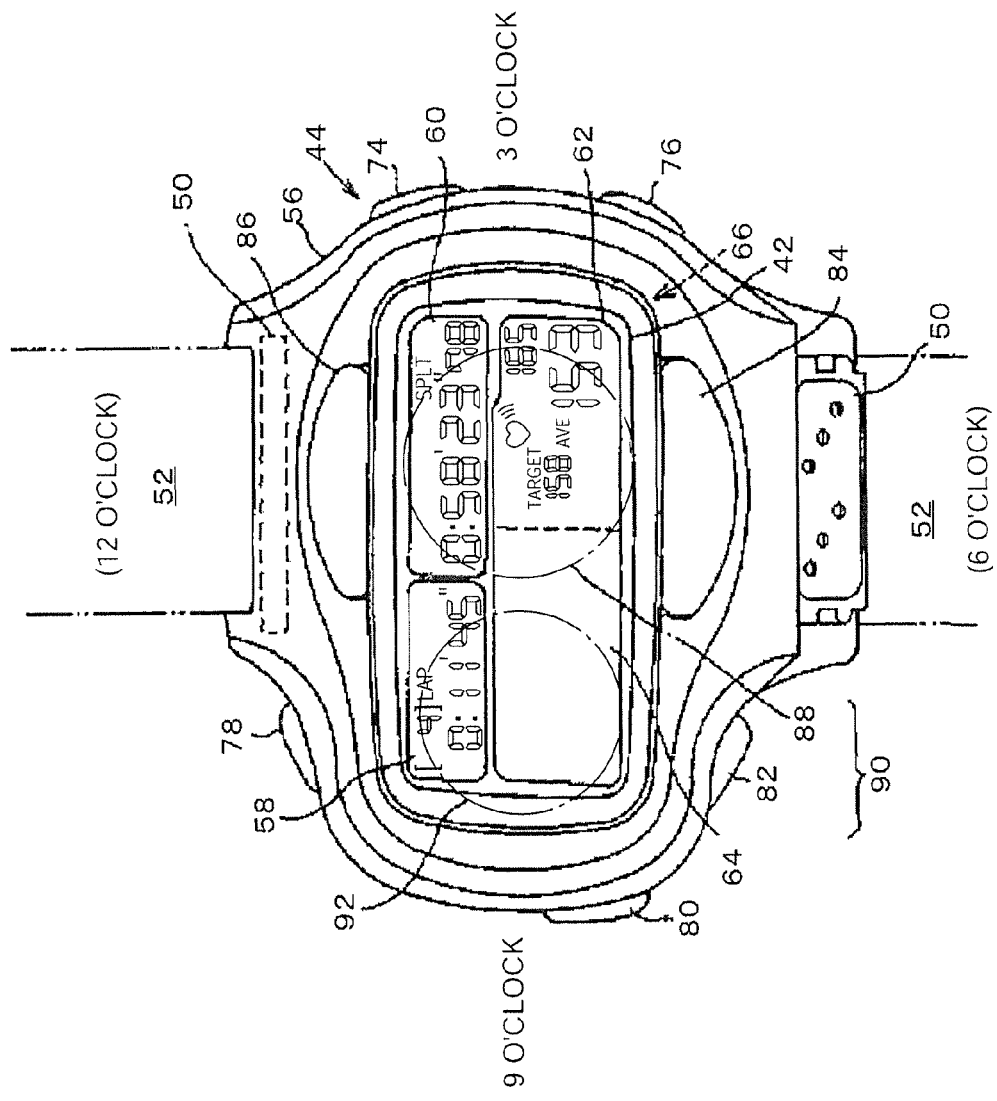
FIG. 5 is a top view of the main body of the pulse detector according to the first embodiment, showing a state where a wrist band, a cable, and the like are removed.

FIG. 5 is a top view of the main body 44 of the pulse detector 2 according to the present embodiment, showing a state where the wrist band 52, the cable 46, and the like are removed. In FIG. 5, the main body 44 includes a watch casing 56 made from a resin. On the top surface of the watch casing 56, an EL backlight-attached liquid crystal display 42 is provided, on which a pace during running and walking, pulse wave information such as the pulse rate, and the like are displayed in addition to the present time and date.

The liquid crystal display 42 has a first segment display region 58 positioned on the top left side of a display surface, a second segment display region 60 positioned on the top right side, a third segment display region 62 positioned on the bottom right side, and a dot display region 64 positioned at the bottom left side. In the dot display region 64, various kinds of information can be displayed graphically.

Inside the watch casing 56, a motion sensor 30 (see FIG. 6) is provided for calculating the pitch. An acceleration sensor or the like can be used as the motion sensor 30.

Moreover, a control unit 66 that performs various kinds of control and data processing is provided in the watch casing 56. This control unit 66 calculates an average pulse rate, a change over time in the variation of the pulse rate from the average pulse rate, and the like based on the detection results (motion signal) by the motion sensor 30 and the detection results (first pulse wave signal) by the pulse wave sensor 10, and if necessary, displays the calculated data on the liquid crystal display 42. Moreover, the control unit 66 transmits the calculated average pulse data corresponding to each calculation time and pulse variation data representing a variation of the pulse rate from the average pulse rate corresponding to the average pulse data to a management center (not shown) through a transceiver circuit 68 (see FIG. 6) and an antenna unit 70 together with an ID code that specifies the pulse detector 2.

In this case, since a timer circuit is also included in the control unit 66, hours and the like are generally displayed on the liquid crystal display 42.

Moreover, an input unit 72 (see FIG. 6) is arranged on the periphery of the watch casing 56 in which button switches 74 to 82 are arranged for performing external operations such as time adjustment and display mode switching. Moreover, the input unit 72 is also arranged on the top surface of the watch casing 56 in which large button switches 84 and 86 are provided.

The pulse detector 2 is powered by a small button-type battery 88 that is included inside the watch casing 56. The cable 46 supplies electrical power from the battery 88 to the pulse wave sensor 10 and transfers the detection results of the pulse wave sensor 10 to the control unit 66 of the watch casing 56.

With the increase in the number of functions provided by the pulse detector 2, there is a need to increase the size of the main body 44. However, since there is a limitation in that the main body 44 should be worn around the wrist, it is difficult to enlarge the main body 44 in the directions of the 6 o'clock and 12 o'clock sides of a wristwatch.

In the present embodiment, the watch casing 56 used in the main body 44 has a horizontally long shape such that the length in the directions of the 3 o'clock and 9 o'clock is longer than the length in the directions of the 6 o'clock and 12 o'clock.

In this case, the wrist band 52 is connected at positions shifted to the 3 o'clock side. Therefore, when seen from the wrist band 52, an extension portion 90 which is different from that on the 3 o'clock side is provided on the 9 o'clock side of the wristwatch. Accordingly, it becomes easier to freely bend the wrist compared to the case of using the watch casing 56 that has a horizontally long shape. Moreover, even when the wrist is bent backwards, the back of a hand will not touch against the watch casing 56.

Inside the watch casing 56, a flat piezoelectric element 92 for generating a buzzing sound is disposed on the 9 o'clock side to the battery 88. Since the battery 88 is heavier than the piezoelectric element 92, the central position of the main body 44 is at a position shifted to the 3 o'clock side. Since the wrist band 52 is connected to the side of the shifted central position, the main body 44 can be worn around the wrist in a stable state. Moreover, since the battery 88 and the piezoelectric element 92 are arranged in a planar direction, the main body 44 can be made thin. In addition to this, although not shown, a battery cover is formed on the rear surface, so that a user can replace the battery 88 easily.

Moreover, the antenna unit 70 for performing communication with the management center is provided inside the watch casing 56.

Figure 6:
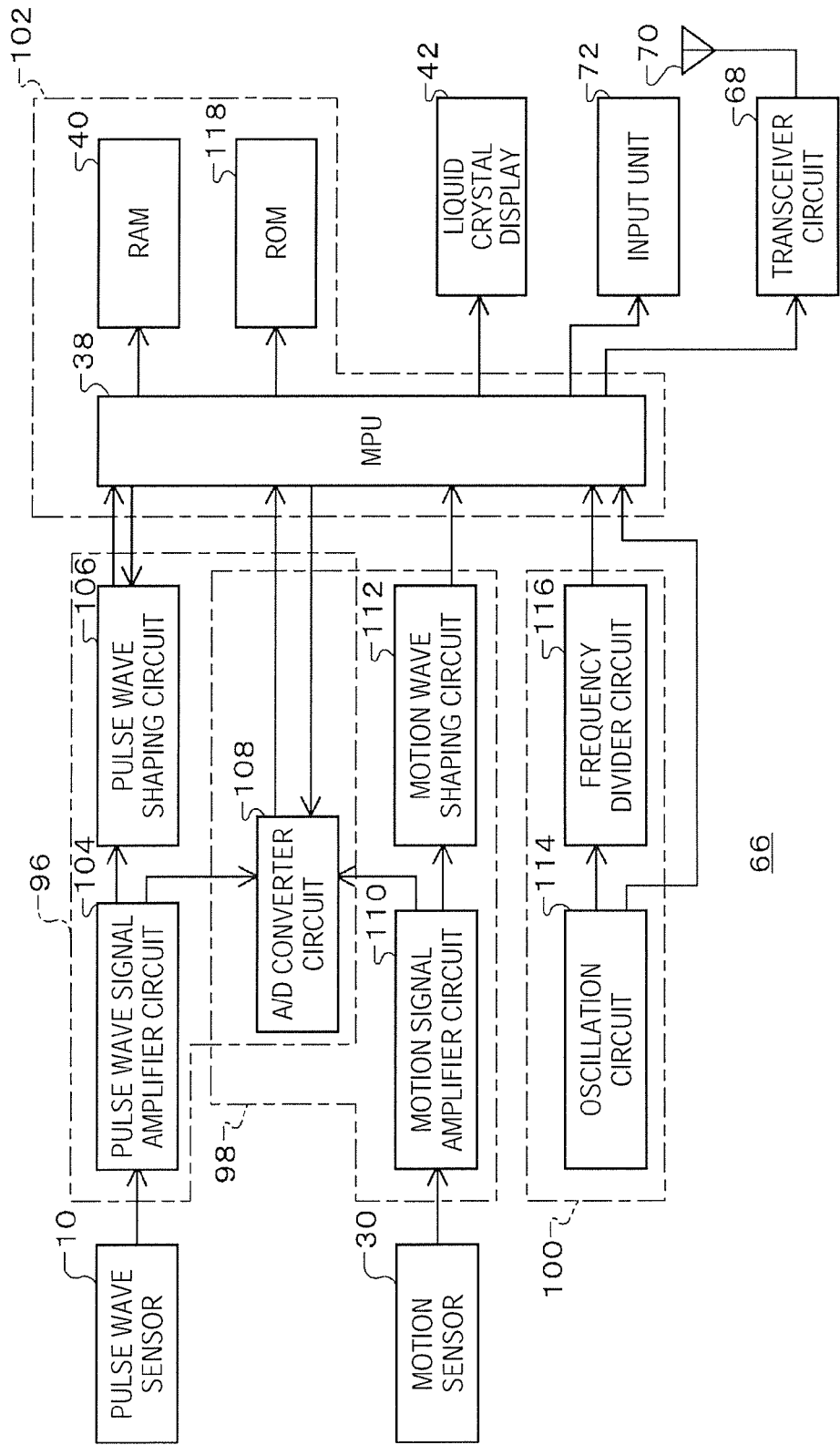
FIG. 6 is a schematic block diagram showing the configurations around a control unit according to the first embodiment.

FIG. 6 a schematic block diagram showing the configurations around the control unit 66 according to the present embodiment.

The control unit 66 is roughly configured to include a pulse wave data processor 96 for calculating the pulse rate or the like based on the results input from the pulse wave sensor 10, a pitch data processor 98 for calculating the pitch based on the results input from the motion sensor 30, a clock generator 100 for generating an operation clock signal, and a controller 102 for controlling the whole of the control unit 66.

The pulse wave data processor 96 roughly includes a pulse wave signal amplifier circuit 104, a pulse wave shaping circuit 106, and an A/D converter circuit 108. Among them, the A/D converter circuit 108 is shared with the pitch data processor 98.

The pulse wave signal amplifier circuit 104 amplifies the first pulse wave signal which is the output of the pulse wave sensor 10 and outputs the amplified first pulse wave signal to the A/D converter circuit 108 and the pulse wave shaping circuit 106.

The pulse wave shaping circuit 106 performs wave-shaping on the amplified pulse wave signal and outputs the resulting signal to the controller 102.

The A/D converter circuit 108 performs A/D conversion on the amplified pulse wave signal and outputs the resulting signal to the controller 102 as pulse wave data.

The pitch data processor 98 roughly includes a motion signal amplifier circuit 110, a motion wave shaping circuit 112, and the A/D converter circuit 108. Among them, the A/D converter circuit 108 is shared with the pulse wave data processor 96 as described above.

The motion signal amplifier circuit 110 amplifies the motion signal which is the output of the motion sensor 30 and outputs the amplified motion signal to the A/D converter circuit 108 and the motion wave shaping circuit 112.

The motion wave shaping circuit 112 performs wave-shaping on the amplified motion signal and outputs the resulting signal to the controller 102.

The A/D converter circuit 108 performs A/D conversion on the amplified motion signal and outputs the resulting signal to the controller 102 as motion data.

The clock generator 100 roughly includes an oscillation circuit 114 and a frequency divider circuit 116.

The oscillation circuit 114 includes a quartz crystal oscillator or the like. The oscillation circuit 114 supplies a clock signal to the controller 102 as a reference operation clock and supplies the clock signal to the frequency divider circuit 116 so that a counter clock signal is generated from the clock signal.

The frequency divider circuit 116 divides the frequency of the supplied clock signal to generate and supply various counter clock signals to the controller 102.

The controller 102 roughly includes the MPU 38, the RAM 40, and a ROM 118. The MPU 38 is connected to the input unit 72, the transceiver circuit 68, and the antenna unit 70 in addition to the liquid crystal display 42 described above.

The MPU 38 controls the whole of the control unit 66, and consequently, the whole of the pulse detector 2 based on a control program stored in the ROM 118.

The RAM 40 temporarily stores various kinds of data including the pulse wave data and the motion data and is used as a work area.

The ROM 118 stores in advance the control program for controlling the whole of the MPU 38, and eventually, the pulse detector 2.

In the above-described present embodiment, the pulse wave signal filtering unit and the filter coefficient setting unit of the pulse detector 2 are realized when the MPU 38 processes the first pulse wave signal data d and the motion signal data in accordance with a predetermined program. For example, the main function of the pulse wave signal filtering unit is to detect the pulse by removing a noise component correlated to the motion from the second pulse wave signal using an adaptive filter which is constructed by an FIR filter or the like. The adaptive filter is a digital filter which is realized when the MPU 38 executes a predetermined program.

Difference from General Adaptive Filter Processing

Generally speaking, adaptive filter processing repeatedly performs processing until the difference data e are minimized (or become equal to or lower than a threshold). In contrast, the adaptive filter used in the present embodiment and adaptive filters for removing body motion components which have been used from the past are those which are also referred to as adaptive notch filters. A notch filter is a filter that divides an input signal into an unnecessary signal and a necessary signal. Thus, an adaptive notch filter is a filter that has a function of changing (namely, adapting) its filter characteristics so as to comply with a desired signal on a real-time basis.

Adaptive Notch Filter Processing Applied to Motion Removing Algorithm

Since the filter output y having correlation with an acceleration signal in the first pulse wave signal is output from the adaptive filter, the difference data e of the heartbeat component can be derived by subtracting this filter output y from the original signal before being input to the adaptive filter.

The filtering computation processing by the adaptive filter can be expressed as follows.

$$Y[i]=\Sigma\{h[k]*Y[i-k]\} \ (i=1 \ to \ n, k=1 \ to \ n)$$

$$E[i]=d[i]-Y[i] \ (i=1 \ to \ n)$$

As the adaptive filter coefficients update processing, an LMS algorithm can be used, for example.

$$h[k]=h[k]+\mu*E[i]*Y[i-k] \ (i=1 \ to \ n, k=1 \ to \ n)$$

In the above equations, n is a filter length (array size), and for example, 64 is used as the filter length, so that the first pulse wave signal and the acceleration signal are subjected to filter processing every 64 samples (that is, the filter length is the number of digital signal samples). Moreover, i is the number of a sample being calculated among n samples (i=1 to n), Y[i] is a component having high correlation with the acceleration signal in the first pulse wave signal (i=1 to n), d[i] is the first pulse wave signal data (sensor output) (i=1 to n), E[i] is the heartbeat signal data (i=1 to n), h[k] is a window of filter coefficients (k=1 to n), and μ is a step size. The larger the step size of a filter, the higher the ability to track changes in a reference signal. The smaller the step size, the higher the stability of the filter though the ability to track decreases.

By performing the above processing with respect to the sample number i=1 to 64, the waveform E[1] to E[64] of the heartbeat signal data can be obtained.

The following is the processing procedure in a general adaptive notch filter.

```
for i=1 to n {
    for k=1 to n {
        (filtering computation processing for sample 1)
    }
    for k=1 to n {
        (filter coefficient update processing)
    }
}
```

Adaptive Notch Filter Processing Introduced in Noise Removal Unit 94 of Present Embodiment By the following computation processing, a signal having high autocorrelation (that is, a signal in which unexpected noise is not contained) in the first pulse wave signal can be obtained.

The filtering computation processing by the adaptive filter can be expressed as follows.

$$Y[i]=\Sigma\{h[k]*Y[i-k-1]\} \ (i=1 \ to \ n, k=1 \ to \ n)$$

(−1 represents the amount of delay processing)

$$E[i]=d[i]-Y[i] \ (i=1 \ to \ n)$$

As the adaptive filter coefficients update processing, an LMS algorithm can be used, for example.

$$h[k]=h[k]+\mu*E[i]*Y[i-k] \ (i=1 \ to \ n, k=1 \ to \ n)$$

In the above equations, n is a filter length (array size), and for example, 64 is used as the filter length, so that the first pulse wave signal and the acceleration signal are subjected to filter processing every 64 samples (that is, the filter length is the number of digital signal samples). Moreover, i is the number of a sample being calculated among n samples (i=1 to n), Y[i] is a component having high autocorrelation (signal A) in the first pulse wave signal (i=1 to n), d[i] is the first pulse wave signal data (sensor output) (i=1 to n), E[i] is a component having low autocorrelation (signal B) in the heartbeat signal (i=1 to n), h[k] is a window of filter coefficients (k=1 to n), and μ is a step size. The larger the step size of a filter, the higher the ability to track changes in a reference signal. The smaller the step size, the higher the stability of the filter though the ability to track decreases.

By performing the above processing with respect to the number of input samples (64), the signal waveform A having high autocorrelation can be obtained as Y[1] to Y[64].

The following is the processing procedure in a general adaptive notch filter.

```
for i=1 to n {
    for k=1 to n {
        (filtering computation processing for sample 1)
    }
    for k=1 to n {
        (filter coefficient update processing)
    }
}
```

FIG. 7A to FIG. 11B are graphs showing the respective signal waveforms and the results of frequency analysis by FFT processing before and after the signal processing in the pulse detector 2. Curves 120*a* to 120*l* on the top of each graph show signal waveforms obtained by connecting points in which data at each sampling point are plotted in a time-sequential manner, and the vertical axis of each graph is a time axis. Moreover, bar graphs 122*a* to 122*l* on the bottom of the graph show the results of frequency analysis, and the horizontal axis is a frequency. These figures show the process of detecting the pulse of a person in a situation where the person in a stationary state starts running suddenly and a body motion has increased abruptly. The signal waveforms 120*a* to 120*l* and the frequency analysis results 122*a* to 122*l* shown in these figures are obtained when the MPU 38 executes processing based on the pulse detection processing algorithm shown in FIG. 2 using the same hardware as the above-described embodiment.

The graphs in FIG. 7A to FIG. 11B show the waveforms 120*a* to 120*l* of signals acquired for 16 seconds at a sampling frequency of 16 Hz and the frequency analysis results 122*a* to 122*l*. FIGS. 7A to 7C are diagrams showing normal-mode output data from the pulse wave sensor 10 of the pulse detector 2 according to the present embodiment, specifically showing the first pulse wave signal data d, the first pulse wave signal data d (signal A), and the first pulse wave signal data d (signal B). More specifically, FIGS. 7A to 7C show the first pulse wave signal data d output from the pulse wave sensor 10 and the signals A and B of the first pulse wave signal data d, respectively. For example, the measurement was performed during resting after exercise, and the pulse rate was calculated to be "97" as the measurement result. FIG. 7A shows the waveform 120*a* of the first pulse wave signal data d. FIG. 7B shows the data of a signal generated based on the motion signal data and the adaptive filter coefficient (h), showing the signal A of the first pulse wave signal data d shown in FIG. 7A. For example, the gain coefficient is "1.0." FIG. 7C shows the component of the signal B obtained by subtracting the signal A from the first pulse wave signal data d in FIG. A. For example, the gain coefficient is "1.0."

FIGS. 8A and 8B show the results of pulse detection processing. FIG. 8A shows pulse signal data when the noise removal unit 94 is not used (see the flow of the related art shown in FIG. 1), and FIG. 8B shows pulse signal data when the noise removal unit 94 of the pulse detector 2 according to the present embodiment is used. Here, the first pulse wave signal data d before the signal processing are the same as the waveforms 120a, 120b, and 120c shown in FIGS. 7A and 7B. FIG. 8A shows the waveform 120d of the pulse signal data when the noise removal unit 94 is not used and the frequency analysis results 122d, and FIG. 83 shows the waveform 120e of the pulse signal data which are the results of the signal processing by the pulse detection algorithm according to the present embodiment and the frequency analysis results 122e.

The combined output of the signals A and B of the first pulse wave signal data d used in FIG. 8B can be expressed as (Output Signal)=(h1×Signal A)+(h2×Signal B) (where, gain coefficients are h1=1.0 and h2=0.5), for example. From the comparison between FIGS. 8A and 8B, an improvement result can be seen from an SN index, for example, which is expressed using a percentage of (the sum of three spectrum values before and after a pulse baseline)/(the sum of all spectrum values). If the index value has increased, it means that the spectrum showing the pulse becomes more prominent and that it becomes easy to specify the pulse.

In FIG. 8A, the improvement result is 33.7% when the noise removal unit 94 is not used. The signal after motion effect removal which is the final signal used for pulse detection is substantially equivalent to the output signal of the pulse wave sensor. In FIG. 83, the improvement result is 37.8% when the noise removal unit 94 is used. The signal after motion effect removal which is the final signal used for pulse detection is substantially equivalent to the output signal of the noise removal unit 94. By using the present embodiment, it is possible to make the spectrum showing the pulse prominent and specify the frequency originating from the pulse.

Figures 9A, 9B, 9C:
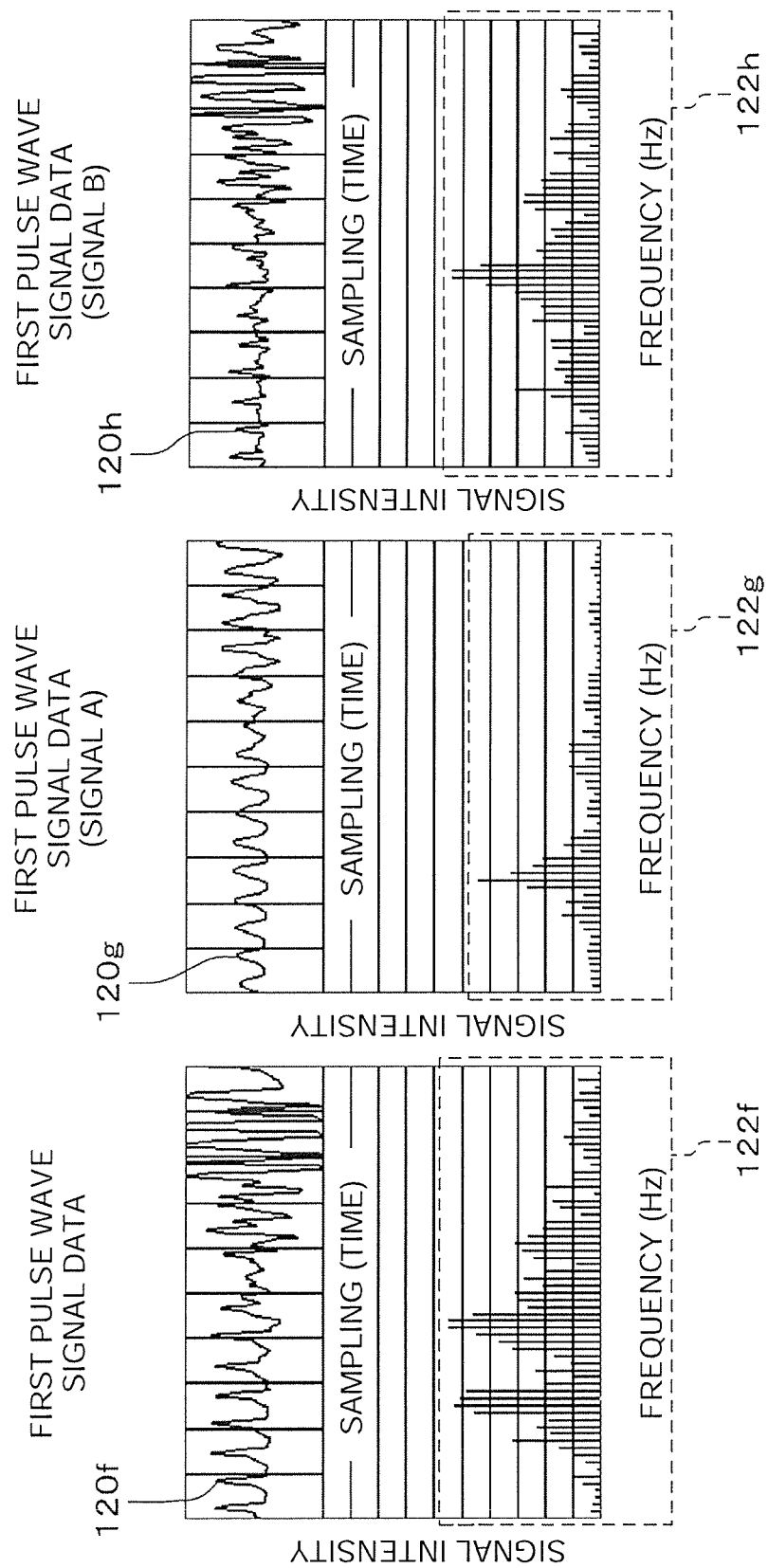

FIGS. 9A to 9C are diagrams showing impact-mode output data from the pulse wave sensor 10 of the pulse detector 2 according to the present embodiment, specifically showing the first pulse wave signal data d, the first pulse wave signal data d (signal A), and the first pulse wave signal data d (signal B). In FIG. 9A, in the waveform 120f of the first pulse wave signal data d, a noise component originating from a body motion is weighted, and therefore, it is difficult to specify the frequency component showing the pulse from the frequency analysis results 122f by the FFT processing. FIG. 9B shows the data of a signal generated based on the motion signal data and the adaptive filter coefficient (h), showing the signal A of the first pulse wave signal data d shown in FIG. 9A. For example, the gain coefficient is "1.0." FIG. 9C shows the signal B obtained by subtracting the signal A from the first pulse wave signal data d shown in FIG. 9A. For example, the gain coefficient is "1.0."

Figure 10B:
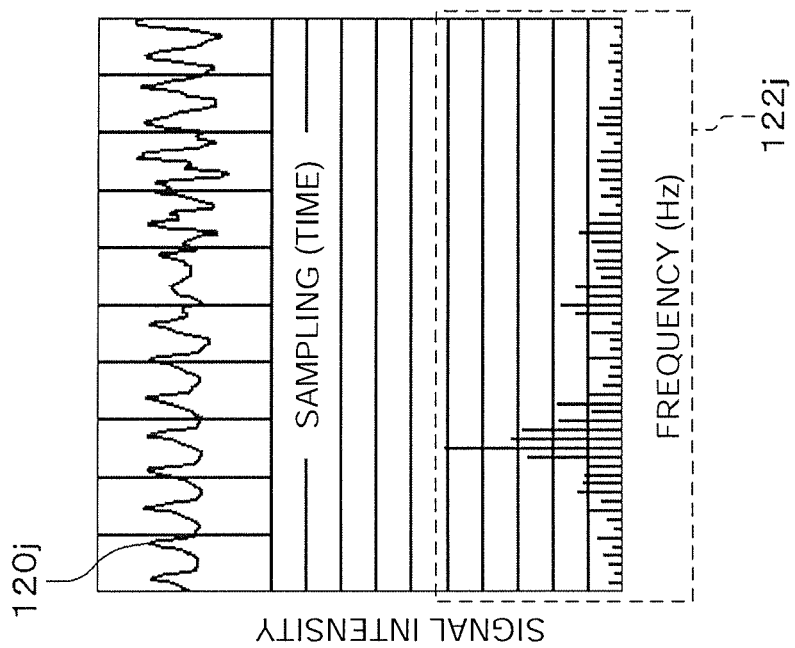
FIG. 10B shows pulse signal data when the excessive-amplitude noise removal unit of the pulse detector according to the first embodiment is used.
Figure 10A:
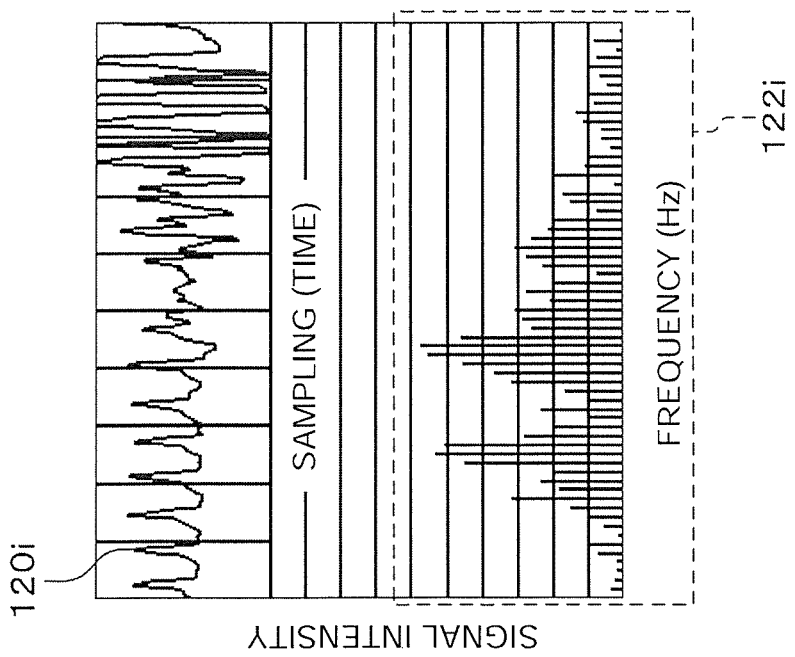
FIG. 10A shows pulse signal data when an excessive-amplitude noise removal unit is not used.

FIGS. 10A and 10B show the results of pulse detection processing. FIG. 10A shows pulse signal data when the noise removal unit 94 is not used (see the flow of the related art shown in FIG. 1), and FIG. 10B shows pulse signal data when the noise removal unit 94 of the pulse detector 2 according to the present embodiment is used. Here, the first pulse wave signal data d before the signal processing are the same as the waveforms 120f, 120g, and 120h shown in FIGS. 9A and 9B. FIG. 10A shows the waveform 120i of the pulse signal data when the noise removal unit 94 is not used and the frequency analysis results 122i, and FIG. 10B shows the waveform 120j of the pulse signal data which are the results of the signal processing by the pulse detection algorithm according to the present embodiment and the frequency analysis results 122j.

The combined output of the signals A and B of the first pulse wave signal data d used in FIG. 10B can be expressed as (Output Signal)=(h1×Signal A)+(h2×Signal B) (where, the first gain coefficients are h1=1.0 and h2=0.5) in a zone with no impact noise, or (Output Signal)=(h1×Signal A)+(h2×Signal B) (where, the second gain coefficients are h1=1.0 and h=0.0) in a zone with impact noise, for example.

In the present embodiment, in the impact mode, resistance to an impact signal is increased (that is, it becomes easy to specify the frequency of pulse waves). Moreover, in the normal mode, a state where abrupt changes in the pulse and motion can be dealt with easily can be maintained while providing a certain degree of impact resistance.

From the comparison between FIGS. 10A and 10B, an improvement result seen from an SN index is 12.7% in FIG. 10A in which the noise removal unit 94 is not used. The signal after motion effect removal which is the final signal used for pulse detection is substantially equivalent to the output signal of the pulse wave sensor. In FIG. 10B, the improvement result is 27.4% when the noise removal unit 94 is used. The signal after motion effect removal which is the final signal used for pulse detection is substantially equivalent to the output signal of the noise removal unit 94. By using the present embodiment, it is possible to make the spectrum showing the pulse prominent and specify the frequency originating from the pulse.

FIGS. 11A and 11B show the first pulse wave signal data d when gain coefficients are used. FIG. 11A shows the second pulse wave signal data d2 when the same gain coefficients are used in the normal mode and the impact mode, and FIG. 11B shows the second pulse wave signal data d2 when the coefficients of the adaptive filter are updated even after the impact mode has started. Here, the first pulse wave signal data d before the signal processing are the same as the waveforms 120f, 120g, and 120h shown in FIGS. 9A and 9B. FIG. 11A shows the waveform 120k of the second pulse signal data d2 when the same gain coefficients are used in the normal mode and the impact mode and the frequency analysis results 122k, and FIG. 11B shows the waveform 120l of the second pulse signal data d2 when the coefficients of the adaptive filter are updated even after the impact mode has started and the frequency analysis results 122l.

The combined output of the signals A and B of the first pulse wave signal data d used in FIG. 11A is fixed to (Output Signal)=(h1×Signal A)+(h2×Signal B) (where, gain coefficients are h1=1.0 and h2=0.5), for example. Here, the signal B component has a gain coefficient of h2=0.5, meaning that it is carried on a signal which was present in a half of the original signal. Therefore, it is desirable to underestimate the signal B component by changing h2 to 0 or smaller values. In this case, the SN value is 19.1%.

In FIG. 11B, with the passage of the sampling time, the adaptive filter becomes adapted to the signal B component. By decreasing the step size which is a unit value of updating the filter coefficients by calculation, it is possible to alleviate the mixing of the signal B. However, there is a possibility that the signal A is also rejected if a change in the trend when the pulse rate keeps changing is not to be kept in track. In this case, the SN value is 14.2%.

In the present embodiment, since an impact noise signal having a high signal level is decreased in the signal A, it is possible to decrease the possibilities of an error or failure in the pulse detection when specifying the frequency component representing the pulse at the time of performing the pulse frequency analysis. Moreover, since the pulse wave frequency analysis is performed after the first pulse wave signal obtained from the pulse wave sensor 10 is divided into the signal component having autocorrelation and the other components, it is possible to alleviate the influence of an unexpected noise signal.

Moreover, it is possible to remove a noise signal caused by a motion of the finger, the wrist, and the like and a noise signal caused by an impact near the finger, the wrist, and the like, which were difficult to remove with the adaptive filter for motion removal according to the related art. Furthermore, since signals having a high signal level with no correlation with the heartbeat component are removed, it is easy to specify the frequency component representing the pulse when performing pulse frequency analysis (that is, it is easy to detect the pulse).

Second Embodiment

Figure 12:
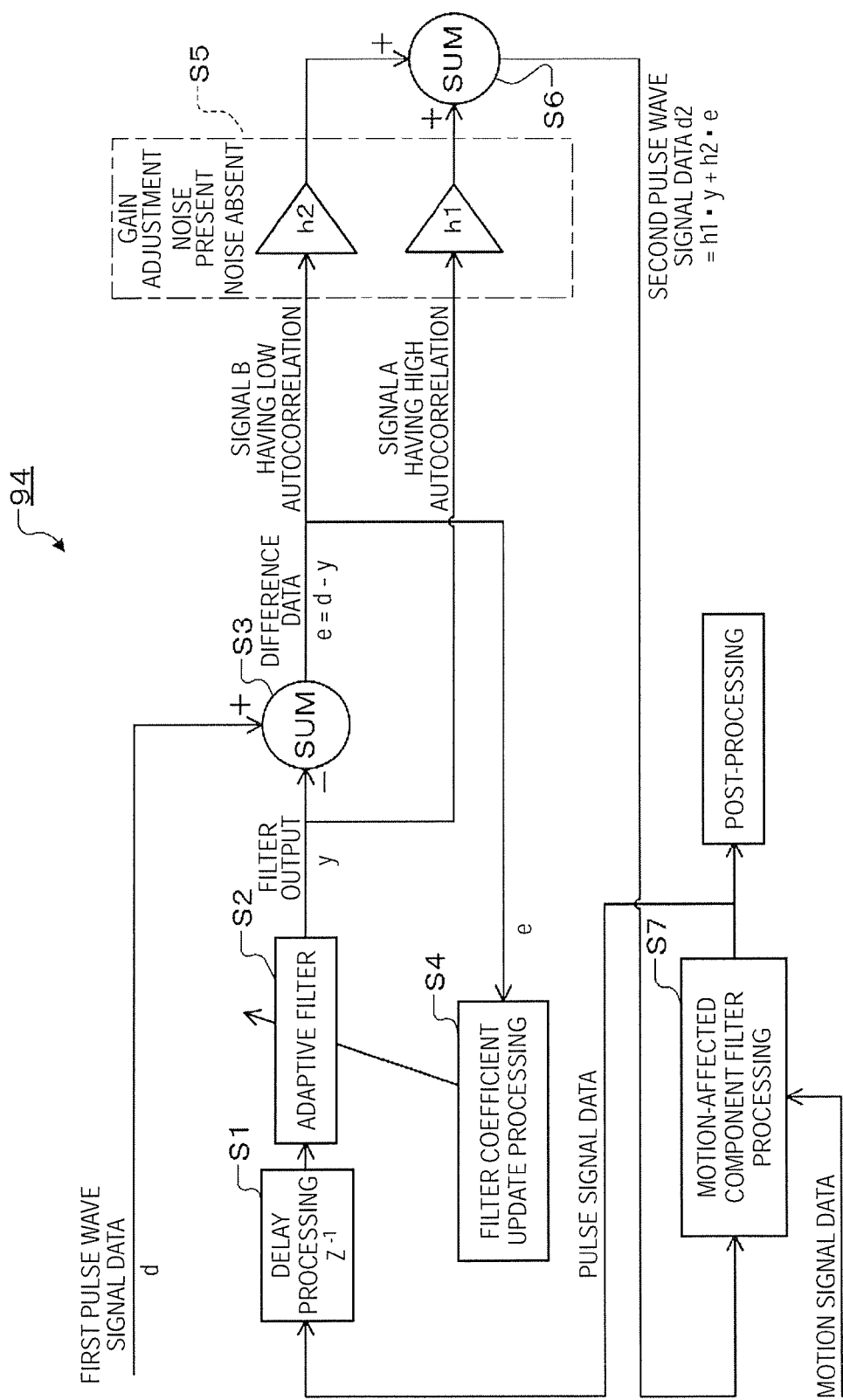
FIG. 12 is a block diagram of processing steps of an excessive-amplitude noise removal unit according to a second embodiment.
Figures 14A, 14B:
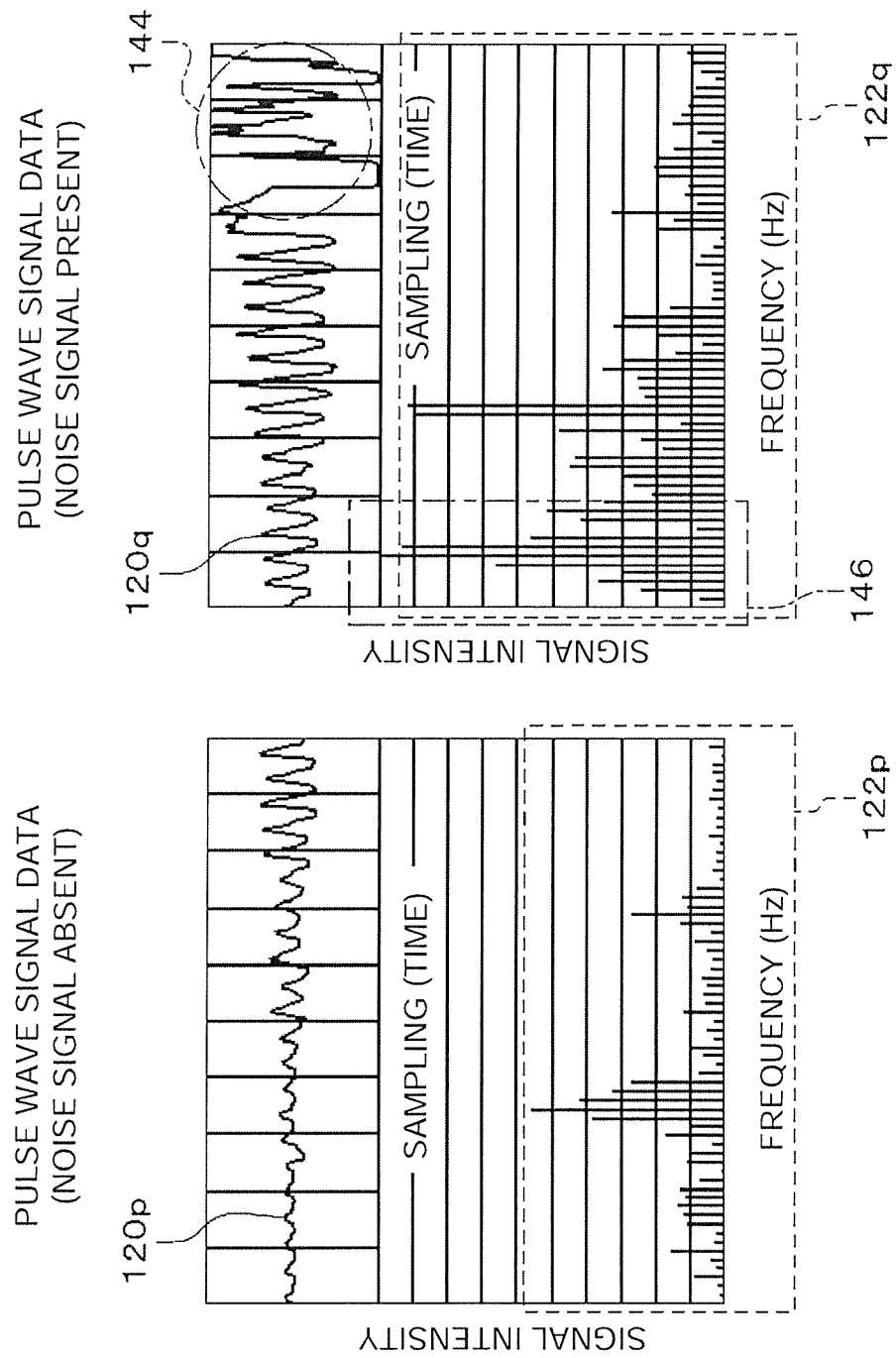
FIG. 14A shows pulse signal data when there is no noise.
FIG. 14B shows pulse signal data when there is noise.

FIG. 12 is a block diagram of processing steps of a pulse detection method in the pulse detector 2 according to the present embodiment. FIG. 13A shows first pulse wave signal data output from the pulse wave sensor 10 of the pulse detector 2, FIG. 13B shows pulse signal data when the noise removal unit 94 is not used (see the flow of the related art shown in FIG. 1), and FIG. 13C shows pulse signal data when the noise removal unit 94 of the pulse detector 2 according to the present embodiment is used. In the present embodiment, the same constituent elements as the first embodiment will be denoted by the same reference numerals, and description thereof will be omitted.

In the present embodiment, pulse signal data (third pulse wave signal) having passed through the filtering unit 28 are input as the reference signal of the noise removal unit 94. The pulse detection method according to the present embodiment includes outputting the pulse signal data which are the output signal of the motion-affected component filter processing as the reference signal of the noise removal unit 94 (step S7) in addition to the respective processing steps (steps S1 to S6) of the first embodiment.

FIG. 13A shows the waveform of the first pulse wave signal data d output from the pulse wave sensor 10 and the frequency analysis results by the FFT processing. In the waveform 120m of the first pulse wave signal data d output from the pulse wave sensor 10, an unexpected noise signal 128 is mixed in addition to a heartbeat signal and a periodic motion signal. Looking at the frequency analysis results 122m by the FFT processing, spectrums having strong power such as the peaks 130, 132, and 134 are present. For example, it can be considered that the peak 130 is the spectrum of an unexpected signal data, the peak 132 is the spectrum of motion signal data, and the peak 134 is the spectrum of a heartbeat component.

FIG. 13B shows the waveform of pulse signal data when signal processing is performed in accordance with a motion removal algorithm of the related art and the frequency analysis results by the FFT processing. In the waveform 120n of the pulse signal data, an unexpected noise signal 136 is mixed in addition to a heartbeat signal and a periodic motion signal. Looking at the frequency analysis results 122n by the FFT processing, although it is possible to remove a signal at a frequency band corresponding to the peak 132 in FIG. 13A, a signal at a frequency band corresponding to the peak 130 is not rejected but is left as a peak 138.

FIG. 13C shows the waveform of pulse signal data when the processing of the processing block diagram shown in FIG. 12 is applied and the frequency analysis results by the FFT processing. In the waveform 120o of the pulse signal data, an unexpected noise signal is not mixed. Looking at the frequency analysis results 122o by the FFT processing, it can be found that both signals at the frequency bands corresponding to the peaks 130 and 132 in FIG. 13A are rejected, and only a signal at a frequency band of a peak 142, namely the peak 134 in FIG. 13A is left.

In the present embodiment, as shown in the processing block diagram of FIG. 12, the pulse signal data having passed through the filtering unit 28 are input as the reference signal of the noise removal unit 94. With this configuration, it is possible to obtain only signals having high correlation with the signal in which motion components are removed as the output of the noise removal unit 94. Moreover, the pulse wave frequency analysis is made easier.

The signal A includes the heartbeat signal component. The signal B includes an abnormal unexpected signal component which contains changes in the bloodstream caused by a motion of a finger or the wrist and changes in the bloodstream caused by a touch on a finger or the wrist, a normal signal component which contains changes in the bloodstream caused by swinging of the arm during walking or jogging.

In the present embodiment, since an impact noise signal having a high signal level is decreased in the signal A, it is possible to decrease the possibilities of an error or failure in the pulse detection when specifying the frequency component representing the pulse at the time of performing the pulse frequency analysis.

The entire disclosure of Japanese Patent Application No. 2009-246211, filed Oct. 27, 2009 is expressly incorporated by reference herein.

What is claimed is:

1. A pulse detector that detects a pulse signal originating from the pulse of a human body, comprising:
    a pulse wave sensor that outputs a first pulse wave signal in which the pulse signal and a noise signal are mixed, wherein the noise signal includes a normal signal having a high autocorrelation and an abnormal noise signal having a low autocorrelation;
    a motion sensor that outputs a motion signal in response to a motion of the human body;
    a first filtering unit that outputs a second pulse wave signal including the pulse signal and the normal noise signal extracted from the first pulse wave signal;
    a second filtering unit that outputs a third pulse wave signal which the normal noise signal has been suppressed using the second pulse wave signal and the motion signal; and
    an analyzing unit that analyzes the third pulse wave signal to obtain a frequency information corresponding to the third pulse wave signal;
    wherein the first filtering unit outputs the second pulse wave signal using the first pulse wave signal and the third pulse wave signal.

2. The pulse detector according to claim 1, wherein
    the first filtering unit generates a first component signal including the pulse signal and the normal noise signal, and a second component signal including the abnormal noise signal based on the first pulse wave signal and the third pulse wave signal, and combines the first component signal and the second component signal with a weight factor to output the second pulse wave signal.

3. The pulse detector according to claim 2, wherein
the weight factor is a set of gain coefficient of the first filtering unit which includes gain coefficients corresponding to the first component signal and the second component signal and is switched to a second set of gain coefficient from a first set of gain coefficient when an amplitude of the first pulse signal has increased over the predetermined threshold.

4. The pulse detector according to claim 2, wherein
the first component signal includes a heartbeat signal component and the normal signal which contains changes in the bloodstream caused by swinging motion of an arm during walking or jogging, and
the second component signal includes an abnormal signal which contains changes in the bloodstream caused by a motion of a finger or a wrist and changes in the bloodstream caused by a touch on a finger or a wrist.

5. The pulse detector according to claim 1, further comprising a band member configured and arranged to be attached to the human body, wherein the pulse wave sensor is coupled to the band member so that the pulse wave sensor is configured and arranged to be attached the human body by attaching the band member to the human body.

6. The pulse detector according to claim 1, further comprising
a display section configured and arranged to display a pulse rate obtained based on analysis of the frequency information corresponding to the third pulse wave signal by the analyzing unit.

7. The pulse detector according to claim 1, further comprising:
a timer circuit; and
a display section configured and arranged to display time based on a signal outputted from the timer circuit.

* * * * *